United States Patent [19]

Kingston et al.

[11] Patent Number: 5,731,336
[45] Date of Patent: Mar. 24, 1998

[54] METHOD FOR TREATING MULTIPLE SCLEROSIS

[75] Inventors: Ann E. Kingston, Camberley, United Kingdom; Jill A. Panetta, Zionsville, Ind.

[73] Assignee: Eli Lilly and Company, Indianapolis, Ind.

[21] Appl. No.: 603,358

[22] Filed: Feb. 20, 1996

Related U.S. Application Data

[63] Continuation of Ser. No. 376,606, Jan. 23, 1995, abandoned.
[51] Int. Cl.$^6$ .................................................. A61K 31/425
[52] U.S. Cl. ........................... 514/369; 514/439; 514/445
[58] Field of Search .................................... 514/369, 439, 514/445, 866

[56] References Cited

U.S. PATENT DOCUMENTS

| | | | |
|---|---|---|---|
| 4,791,126 | 12/1988 | Tanouchi et al. | 514/369 |
| 4,831,045 | 5/1989 | Tanouchi et al. | 514/369 |
| 4,897,406 | 1/1990 | Inoue et al. | 548/183 |
| 4,971,996 | 11/1990 | Shiraishi et al. | 514/521 |
| 5,116,855 | 5/1992 | Inoue et al. | 277/34 |
| 5,158,966 | 10/1992 | Lafferty et al. | 514/369 |
| 5,216,002 | 6/1993 | Gidda et al. | 514/369 |
| 5,356,917 | 10/1994 | Panetta. | |
| 5,362,733 | 11/1994 | Backstrom. | |

FOREIGN PATENT DOCUMENTS

| | | | |
|---|---|---|---|
| 0 047 109 | 3/1982 | European Pat. Off. | 277/20 |
| 0 211 670 | 2/1987 | European Pat. Off. | |
| 0 343 643 | 11/1989 | European Pat. Off. | |
| 0 391 644 | 10/1990 | European Pat. Off. | 277/14 |
| 2-300119 | 2/1990 | Japan | 31/12 |
| 2 249 788 | 5/1992 | United Kingdom | 277/36 |

OTHER PUBLICATIONS

Chemical Abstracts, AN 1990:491084, Prosiegel et al., Jan. 1990.

Chemical Abstracts, AN 1989:185585, Prosiegel et al., Jan. 1989.

Chemical Abstracts, AN 1989: 433306, Panetta et al., Jan. 1989.

Mohan, et al., *Indian Drugs*, Dec. 1983, 90–95.

Katsumi, et al., *Chemical & Pharmaceutical Bulletin*, vol. 34, No. 4, Apr. 1986, pp. 1619–1627.

Patent Abstracts of Japan, 11(206) (C–433) [2653] 1987, abstracting 62–29570.

J. Neuroimmunol. (1994), 50(1), 35–42.

*Primary Examiner*—Keith MacMillan
*Attorney, Agent, or Firm*—Arleen Palmberg; Douglas J. Taylor; David E. Boone

[57] ABSTRACT

Provided is a method of treating multiple sclerosis employing certain aryl-substituted rhodanines.

20 Claims, No Drawings

METHOD FOR TREATING MULTIPLE SCLEROSIS

This application is a continuation of application Ser. No. 08/376,606, filed on Jan. 23, 1995 abandoned.

BACKGROUND OF THE INVENTION

This invention provides a method of treating multiple sclerosis in mammals.

Multiple sclerosis was first described as a clinical entity in 1868. Clinically, it is a highly variable disease, which usually begins between the second and fifth decades of life. The most common signs of multiple sclerosis are sensory and visual motor dysfunction. In the chronic form the patient has periods of remission, but with each remission there is greater neurological dysfunction.

Macroscopically, multiple sclerosis involves lesions of 1 to 4 cm called plaques scattered throughout the white matter of the central nervous system. Microscopically, the disease is characterized by a breakdown of the nervous system's myelin sheath. There is also a loss of myelin basic protein in the area of the lesions.

The etiology and pathogenesis of multiple sclerosis remains obscure. Both chronic infectious agents and auto-immunity have been involved and, in fact, both might be important. Meanwhile, the need continues for safer, better calibrated drugs which will either slow the process of neurodegeneration associated with multiple sclerosis or even prevent such neurodegeneration altogether.

It is an object of this invention to provide a new method for treating multiple sclerosis, which method comprises administering a compound selected from among certain aryl-substituted rhodanine derivatives of the general formula.

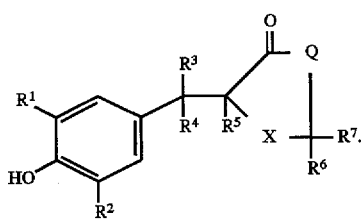

The present method provides for safe and efficacious treatment of multiple sclerosis by slowing (or, quite possibly, preventing) the process of neurodegeneration associated with such disease.

The method of the present invention employs certain aryl-substituted rhodanine derivatives of the general formula set forth above. Such compounds are known in the art (see for example European Patent Applications 211,670, 587,377 and 391,644 and U.S. Pat. Nos. 5,158,966 and 5,216,002) as being useful for treating inflammation, arthritis, Type I diabetes, Inflammatory Bowel Disease, hyperglycemia, Alzheimers disease and muscular dystrophy and for preventing ischemia-induced cell damage.

The aryl-substituted rhodanines employed in the method of the present invention have not heretofore been used to treat multiple sclerosis in mammals. The known activities of such compounds, as set forth above, in no way suggest the method of the present invention. Accordingly, an object of the present invention is to provide a new pharmacological use for certain known rhodanine derivatives.

Other objects, features and advantages of the present invention will become apparent from the subsequent description and the appended claims.

SUMMARY OF THE INVENTION

The present invention provides a method of treating multiple sclerosis in a mammal in need of such treatment, which comprises administering to said mammal a therapeutically effective amount of a compound, or pharmaceutically acceptable salt thereof, of the formula (I)

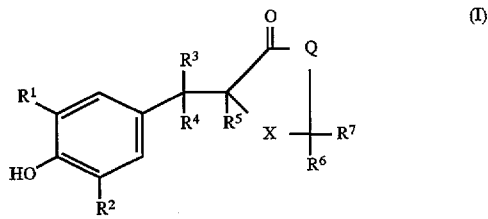

wherein:

$R^1$ and $R^2$ are each independently hydrogen, $C_1$–$C_6$ alkyl, $C_1$–$C_6$ alkoxy, $C_2$–$C_6$ alkenyl, $C_2$–$C_6$ alkynyl or

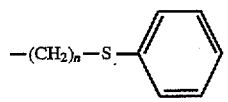

where n is an integer from 0 to 3, both inclusive;

$R^3$ is hydrogen or $C_1$–$C_6$ alkyl;

$R^4$ and $R^5$ are each hydrogen or when taken together form a bond;

$R^6$ and $R^7$ are each hydrogen or when taken together are =S, or when one of $R^6$ or $R^7$ is hydrogen the other is —$SCH_3$;

X is

where m is 0, 1 or 2;

Q is —O— or —$NR^8$; and $R^8$ is hydrogen, $C_1$–$C_6$ alkyl, $C_3$–$C_8$ cycloalkyl, $C_2$–$C_6$ alkenyl, —$SO_2CH_3$ or —$(CH_2)_n$—Y, where n is an integer from 0 to 3, both inclusive, and Y is cyano, $OR^9$,

tetrazolyl, —$NR^{11}R^{12}$, —SH, —$S(C_1$–$C_4$ alkyl) or

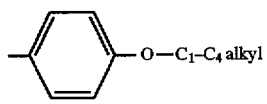

where $R^9$ is hydrogen, $C_1$–$C_4$ alkyl, tosyl or

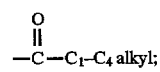

$R^{10}$ is hydroxy, $C_1$–$C_4$ alkyl, $C_1$–$C_4$ alkoxy or —$NH_2$; $R^{11}$ and $R^{12}$ are each independently hydrogen, $C_1$–$C_6$ alkyl, $C_2$–$C_6$ alkenyl, $C_2$–$C_6$ alkynyl, —$(CH_2)_q OH$, —$(CH_2)_q N(C_1$–$C_4$ alkyl$)_2$, —$(CH_2)_q S(C_1$–$C_4$ alkyl) or

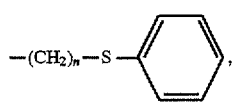

where q is an integer from 1 to 6, both inclusive, and n is as defined above; or $R^{11}$ and $R^{12}$ taken together form a morpholinyl, piperidinyl, piperazinyl or N-methylpiperazinyl ring.

DETAILED DESCRIPTION OF THE INVENTION

As used herein, the term "$C_1$–$C_6$ alkyl" refers to straight and branched chain aliphatic radicals of 1 to 6 carbon atoms, both inclusive, such as methyl, ethyl, propyl, isopropyl, butyl, isobutyl, sec-butyl, tert-butyl, n-pentane, isopentane, n-hexane, isohexane and the like. The term "$C_1$–$C_6$ alkyl" includes within its definition the term "$C_1$–$C_4$ alkyl".

The term "$C_1$–$C_6$ alkoxy" refers to alkyl radicals of 1 to 6 carbon atoms, both inclusive, attached to the remainder of the molecule by oxygen and includes methoxy, ethoxy, propoxy, isopropoxy, butoxy, isobutoxy, sec-butoxy, tert-butoxy, pentoxy, hexoxy and the like. The term "$C_1$–$C_6$ alkoxy" includes within its definition the term "$C_1$–$C_4$ alkoxy".

The term "$C_2$–$C_6$ alkenyl" refers to straight and branched chain radicals of 2 to 6 carbon atoms, both inclusive, having a double bond. As such, the term includes ethylene, propylene, isopropylene, 1-butene, 2-butene, 2-methyl-1-propene, 1-pentene, 2-pentene, 2-methyl-2-butene and the like.

The term "$C_2$–$C_6$ alkynyl" refers to straight and branched chain radicals of 2 to 6 carbon atoms, both inclusive, having a triple bond. As such, the term includes acetylene, propyne, 1-butyne, 2-butyne, 1-pentyne, 2-pentyne, 3-methyl-1-butyne, 1-hexyne, 2-hexyne, 3-hexyne and the like.

The term "$C_3$–$C_8$ cycloalkyl" refers to saturated alicyclic rings of 3 to 8 carbon atoms, both inclusive, such as cyclopropyl, methylcyclopropyl, cyclobutyl, cyclopentyl, cyclohexyl and cyclooctyl.

Compounds of formula I wherein Q is —$NR^8$ and $R^8$ is other than $C_2$–$C_6$ alkenyl or —$SO_2CH_3$ and Y is other than cyano, tetrazolyl, —SH or —S($C_1$–$C_4$ alkyl) are preferred for use in the method of treating multiple sclerosis of the present invention. Of this preferred group of compounds, somewhat more preferred are those compounds of formula I wherein $R^1$ and $R^2$ are each $C_1$–$C_6$ alkyl, $C_1$–$C_6$ alkoxy or

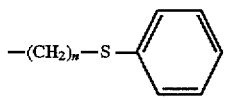

(n being 1, 2 or 3);
$R^3$ is hydrogen, $R^4$ and $R^5$ are each hydrogen or when taken together form a bond; $R^6$ and $R^7$ are each hydrogen or when taken together are =S; X is

where m is 0; Q is —$NR^8$ and $R^8$ is as defined for the preferred group of compounds. Of this somewhat more preferred group of compounds, particularly preferred compounds for use in treating multiple sclerosis, as set forth herein, are those compounds wherein $R^1$, $R^2$, $R^3$, $R^4$, $R^5$, $R^6$, $R^7$, Q, X and m are as set forth immediately above, and $R^8$ is hydrogen, $C_1$–$C_6$ alkyl or —$(CH_2)_n$—Y, where n is 0, 1 or 2 and Y is $OR^9$ ($R^9$ being hydrogen or $C_1$–$C_4$ alkyl) or —$NR^{11}R^{12}$ [$R^{11}$ and $R^{12}$ each being independently hydrogen, $C_1$–$C_6$ alkyl or —$(CH_2)_qOH$, where q is 1, 2 or 3].

Of these particularly preferred compounds, especially preferred compounds for use in the method of the present invention are those compounds wherein $R^1$ and $R^2$ are independently $C_1$–$C_6$ alkyl (and, in particular, 1,1-dimethyethyl) or

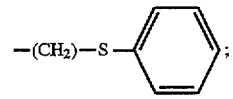

$R^6$ and $R^7$ are hydrogen or when taken together are =S; $R^4$ and $R^5$ taken together form a bond; X is

where m is 0; Q is —$NR^8$ and $R^8$ is hydrogen, $C_1$–$C_4$ alkyl or —$(CH_2)_n$—Y where n is 0, 1 or 2 and Y is —$NR^{11}R^{12}$ [$R^{11}$ and $R^{12}$ each being independently hydrogen, methyl or —$(CH_2)_qOH$, where q is 2] or $OR^9$ ($R^9$ being hydrogen). Of these especially preferred compounds substantially preferred are those compounds wherein $R^8$ is $C_1$–$C_4$ alkyl and, in particular, methyl.

The most preferred compounds for use in the method of treating multiple sclerosis provided herein are 5-[[3,5-bis(1,1-dimethylethyl)-4-hydroxyphenyl]methylene]-3-methyl-4-thiazolidinone; 5-[[3,5-bis(1,1-dimethylethyl)-4-hydroxyphenyl]methylene]-3-(dimethylamino)-4-thiazolidinone; 5-[[3,5-bis(1,1-dimethylethyl)-4-hydroxyphenyl]methylene]-3-(methylamino)-4-thiazolidinone; 5-[[3,5-bis(1,1-dimethylethyl)-4-hydroxyphenyl]methylene]-3-(2-hydroxyethyl)-4-thiazolidinone; 5-[[3,5-bis(1,1-dimethylethyl)-4-hydroxyphenyl]methylene]-3-amino-4-thiazolidinone; 5-[[3,5-bis(1,1-dimethylethyl)-4-hydroxyphenyl]methylene]-3-[(2-hydroxyethyl)amino]-4-thiazolidione; and 4-[[3,5-bis(1,1-dimethylethyl)-4-hydroxyphenyl]methylene]-1,3-oxothiolan-5-one.

Further typical examples of compounds of formula I which are useful in treating multiple sclerosis according to this invention include:

5-[[3,5-bis(1,1-dimethylethyl)-4-hydroxyphenyl]
methylene]-3-(3-methoxypropyl)-2-thioxo-4-thiazolidinone 5-[[3,5-bis(1,1-dimethylethyl)-4-hydroxyphenyl]
methylene]-3-[(2-ethylthio)ethyl]-4-thiazolidinone 5-[[3,5-bis(1,1-dimethylethyl)-4-hydroxyphenyl]methyl]-3-(methylthiomethyl)-4-thiazolidinone 3-acetyl-5-[[3,5-bis(1,1-dimethylethyl)-4-hydroxyphenyl]
methylene]-4-thiazolidinone 5-[[3,5-bis(1,1-dimethylethyl)-4-hydroxyphenyl]methyl]-3-
[N-methyl,N-(1-methylethyl)amino]-4-thiazolidinone 5-[[3,5-bis(1,1-dimethylethyl)-4-hydroxyphenyl]
methylene]-3-[N-methyl,N-(1-methylethyl)amino]-4-thiazolidinone 5-[4-hydroxybenzal]rhodanine 5-(4-hydroxy-3-methoxybenzylidene)rhodanine 5-[(4-hydroxy-3,5-dipropylphenyl)methylene]-3-[2-(dimethylamino)ethyl]-4-thiazolidinone 5-[[3,5-bis(1-methylpropyl)-4-hydroxyphenyl]methylene]-3-methyl-4-thiazolidinone 5-[[3,5-dimethyl-4-hydroxyphenyl]methylene]-3-methyl-4-thiazolidinone 5-[[3,5-bis(1,1-dimethylethyl)-4-hydroxyphenyl]methylene]-3-(methylsulfonyl)-4-thiazolidinone 5-[[4-hydroxy-3,5-bis(1,1-dimethylethyl)phenyl]methylene]-3-(propylamino)-4-thiazolidinone 3-amino-5-[[3,5-bis(1,1-dimethylethyl)-4-hydroxyphenyl]methylene]-2-thioxo-4-thiazolidinone 5-[(4-hydroxy-3,5-dimethoxyphenyl)methylene]-3-methyl-2-thioxo-4-thiazolidinone 5-[(3,5-di-2-propenyl-4-hydroxyphenyl)methylene]-3-[2-(dimethylamino)ethyl]-4-thiazolidinone 5-[(4-hydroxy-3,5-dimethoxyphenyl)methylene]-3-methyl-2-thioxo-4-thiazolidinone 5-[[3,5-diethenyl-4-hydroxyphenyl]methylene]-3-(3-methoxypropyl)-2-thioxo-4-thiazolidinone 5-[[3,5-bis(4-pentyne)-4-hydroxyphenyl]methyl]-3-ethylamino-4-thiazolidinone 5-[[3-ethylthiophenyl-4-hydroxy-5-methylphenyl]methylene]-2-thioxo-4-thiazolidinone 5-[[3-(2-butene)-4-hydroxy-5-isopropoxyphenyl]methyl]-3-(3-diethylaminopropyl)-4-thiazolidinone 5-[[3-(2-propenyl)-4-hydroxy-5-(1,1-dimethylethyl)phenyl]methylene]-3-cyclohexyl-4-thiazolidinone 5-[[3,5-(methylthiophenyl)-4-hydroxyphenyl]methylene]-3-propyl-2-thioxo-4-thiazolidinone 5-[[3-(3-methyl-1-butene)-4-hydroxy-5-propylphenyl]methylene]-3-ethylcyano-4-thiazolidinone 5-[[3-(2-propenyl)-4-hydroxy-5-methoxyphenyl]methyl]-3-ethoxy-4-thiazolidinone 5-[[3,5-di-2-propenyl)-4-hydroxyphenyl]methylene]-3-(methylaminomethyl)-2-thioxo-4-thiazolidinone 5-[[3,5-bis(1,1-dimethylethyl)-4-hydroxyphenyl]methylene]-2-thioxo-4-thiazolidinone 5-[[3,5-bis(1,1-dimethylethyl)-4-hydroxyphenyl]methylene]-4-thiazolidinone 5-[[3,5-bis(1,1-dimethylethyl)-4-hydroxyphenyl]methyl]-4-thiazolidinone 5-[[3,5-bis(1,1-dimethylethyl)-4-hydroxyphenyl]methyl]-2-thioxo-4-thiazolidinone 5-[[3,5-bis(1-methylethyl)-4-hydroxyphenyl]methylene]-3-methyl-4-thiazolidinone The aryl-substituted rhodanine derivatives of formula I are either known in the art or may be prepared by any of a number of well-known procedures. For example, Teuber et al., *Leibigs Ann. Chem.*, 757 (1978) disclose 5-[[3,5-bis(1,1-dimethylethyl)-4-hydroxyphenyl]methylene]-2-thioxo-4-thiazolidinone (referred to in the following discussion as Compound A). The compound is prepared by reacting 3,5-di-tert-butyl-4-hydroxybenzaldehyde with rhodanine at reflux temperature in glacial acetic acid using fused sodium acetate as catalyst. 5-[[3,5-Bis(1,1-dimethylethyl)-4-hydroxyphenyl]methylene]-4-thiazolidinone (Compound B), 5-[[3,5-bis(1,1-dimethylethyl)-4-hydroxyphenyl]methyl]-4-thiazolidinone (Compound C) and 5-[[3,5-bis(1,1-dimethylethyl)-4-hydroxyphenyl]methyl]-2-thioxo-4-thiazolidinone (Compound D) can be prepared from Compound A as follows.

When Compound A is subjected to catalytic hydrogenation, one obtains both Compounds B and C. The relative proportions obtained depend upon the temperature, pressure, and duration of hydrogenation, the solvent employed and the particular catalyst used. For example, when Compound A is treated with 5% palladium on carbon in ethanol at 100° C. for approximately 18 hours, the relative ratios of Compound B:C are approximately 60:40. Alternatively, these transformations may be accomplished by heating Compound A in a mixture of hydrochloric acid and an alcohol, such as ethanol, in the presence of zinc. Reduction of the thione without affecting the benzylic double bond may be accomplished by heating the thione with a reducing agent such as tri-n-butyl tin hydride in a non-reactive solvent, such as toluene, and preferably in the presence of a free radical initiator, such as azobisisobutyronitrile. However, for such reduction to work, an N-substituted rhodanine substrate (i.e., $R^8$ cannot be hydrogen) must be employed.

The transformation of Compound A to D may be accomplished by a variety of methods known in the art. A preferred method is that taught by Nakamura et al., *Tetrahedron Letters*, 25, 3983 (1984). In this reaction, Compound A is treated with a dihydropyridine such as diethyl 2,6-dimethyl-1,4-dihydro-3,5-pyridinedicarboxylate in the presence of silica gel. The reaction is best carried out in the presence of a nonreactive solvent such as benzene or toluene, preferably under an inert atmosphere. The reaction may be accomplished at temperatures from about 25° C. up to the reflux temperature of the mixture. At the preferred temperature of approximately 80° C., the reaction is essentially complete after 12–18 hours.

Other thiazolidinones may, depending on the values selected for the various substituents, be prepared in an analogous fashion. For example, compounds of formula I wherein Q is $NR^8$ and $R^8$ is hydrogen, $C_1$–$C_6$ alkyl, $C_3$–$C_8$ cycloalkyl or —(CH2)$_n$—Y, where n is as defined for formula I, and Y is cyano or $NR^{11}R^{12}$ where $R^{11}$ and $R^{12}$ are each independently hydrogen or $C_1$–$C_6$ alkyl, may be prepared by the method of Teuber et al. described above, employing the appropriate N-substituted rhodanine and $R^1$, $R^2$-substituted-4-hydroxy-benzaldehyde. Alternatively, rhodanine may be used for the condensation with the aldehyde to form those species wherein Q is $NR^8$ and $R^8$ is hydrogen, followed by alkylation with the appropriate $R^8$ containing halide, such as an iodide or bromide, to provide the corresponding N-substituted derivative; i.e., those compounds of formula I in which Q is $NR^8$ and $R^8$ is $C_1$–$C_6$ alkyl, $C_2$–$C_6$ alkenyl, $C_3$–$C_8$ cycloalkyl or —(CH$_2$)$_n$—Y, where Y is cyano, $OR^9$, —SH, —S($C_1$–$C_4$ alkyl), $NR^{11}R^{12}$ or

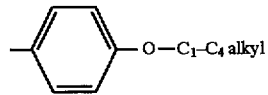

and n, $R^9$, $R^{11}$ and $R^{12}$ are as defined for formula I. The alkylation is usually accomplished in an inert solvent such as tetrahydrofuran (THF) or dimethylformamide (DMF) and in the presence of a strong base such as sodium hydride. In a similar fashion, as is well-known in the art, rhodanine may be used for condensation with the aldehyde forming those species wherein Q is $NR^8$ and $R^8$ is hydrogen, followed by substitution with the appropriate $R^8$ containing halide to provide N-substituted derivatives of formula I in which $R^8$ is —(CH$_2$)$_n$—Y and Y is

where n and $R^{10}$ are as defined for formula I.

Compounds of formula I wherein Q is $NR^8$ and $R^8$ is —(CH$_2$)$_n$—Y (Y is $OR^9$ or $NR^{11}R^{12}$, wherein $R^9$ is hydrogen, acetyl or tosyl and $R^{11}$ and $R^{12}$ are as defined for formula I) may also be prepared according to the following reaction scheme:

may then be transformed into additional compounds of formula I upon treatment with an appropriate $HNR^{11}R^{12}$ amine, where $R^{11}$ and $R^{12}$ are as stated in the preceeding

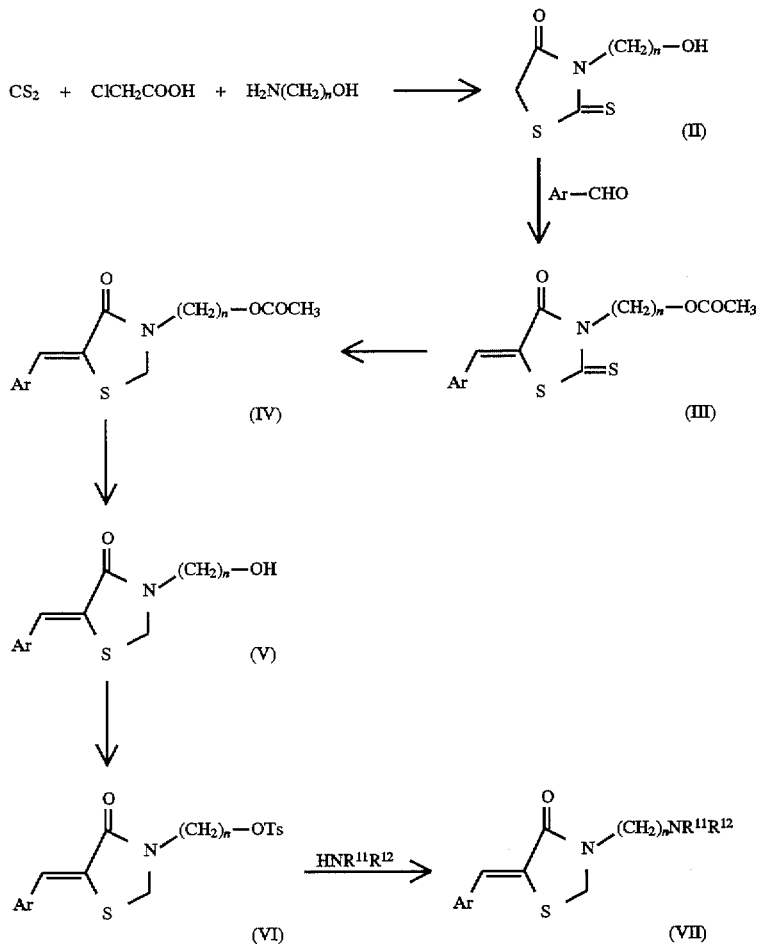

where Ts=Tosyl; Ar=

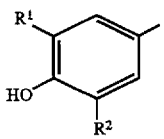

A hydroxyalkyl rhodanine II is prepared by condensing carbon disulfide, chloroacetic acid, and the appropriate hydroxyalkylamine by standard techniques. When condensed with the appropriate $R^1$, $R^2$-substituted-4-hydroxybenzaldehyde as described above, the resulting product is the condensed 2-thioxo-4-thiazolidinone III which has been transformed into the acetyl derivative. The thioxo compound may optionally be converted to the methylene compound of formula IV as described above. The acetyl group of intermediate IV may be removed upon treatment with aqueous ammonia in a solvent such as acetonitrile to provide compound V (i.e., the compound of formula I wherein Q is $NR^8$ and $R^8$ is —(CH$_2$)$_n$—Y where Y is $OR^9$ and $R^9$ is hydrogen). The hydroxy compound V is then converted to the tosyl derivative VI upon treatment with p-toluenesulfonyl chloride in pyridine, preferably at a temperature of around 0° C. The versatile tosyl intermediate VI paragraph. This latter transformation is best accomplished by allowing VI to react in the presence of a molar excess of the amine. Once again, a solvent such as acetonitrile is useful for accomplishing this transformation.

The corresponding 1,3-oxothiolan-5-ones of formula I may be prepared from β-(3,5-di-t-butyl-4-hydroxyphenyl)-α-mercaptoacrylic acid (VIII). Compound VIII may be treated with carbon disulfide to prepare the thione analog (Q is —O—, $R^6$ and $R^7$ are=S), while reaction of VIII with formic acid provides the corresponding desthione (Q is —O—, $R^6$ and $R^7$ are each hydrogen). Compound VIII can be prepared by known methods (see, e.g., Campaigne et al., *J. Org. Chem.*, 26, 359 (1961); id., 26, 1326 (1961); Chakrabarti, et al., *Tetrahedron*, 25(14), 2781 (1969)), or upon heating Compound A with dilute aqueous base.

Compounds of formula I wherein Q is $NR^8$ and $R^8$ is —(CH$_2$)$_n$—Y (n=0) and Y is $NR^{11}R^{12}$, where $R^{11}$ and $R^{12}$ are as defined for formula I, may be prepared according to the following reaction sequence:

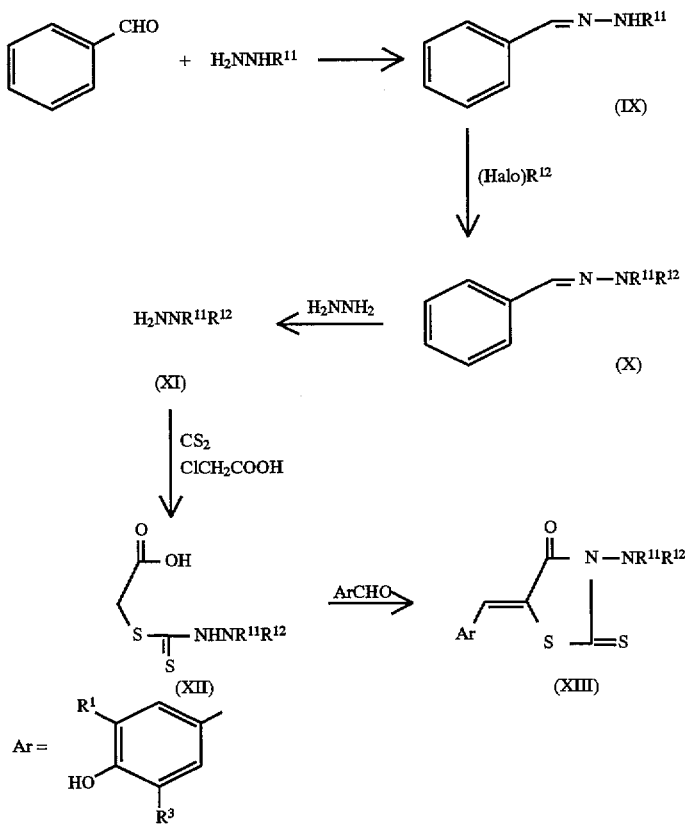

The $R^{11}$-substituted hydrazine is treated with benzaldehyde in an alcoholic (preferably methanol) solvent to yield intermediate IX which, in turn, is reacted with the appropriate $R^{12}$-halide in the presence of triethylamine and acetonitrile to render intermediate X. X is then treated with hydrazine to render the $R^{11},R^{12}$-hydrazine, XI. XI may alternatively be prepared by reducing a nitroso-$R^{11}R^{12}$ amine using zinc dust and acetic acid or aluminum and a strong base. The nitroso-$R^{11}R^{12}$ amine itself is prepared from an $R^{11},R^{12}$ amine as described in J. Am. Chem. Soc. 77, 790 (1955) by treatment with sodium nitrite in HCl. XI is then treated with carbon disulfide, chloroacetic acid and triethylamine to yield intermediate XII. Condensation of XII with the appropriate $R^1,R^2$-substituted-4-hydroxybenzaldehyde (i.e., ArCHO) renders XIII. As described previously, the thione may be reduced by treatment with a reducing agent such as tri-n-butyl tin hydride in a non-reactive solvent such as toluene, preferably in the presence of a free radical initiator such as azobisisobutyronitrile. Preparation of the species wherein one of $R^{11}$ or $R^{12}$ is hydrogen may be effected before or after reduction of the thione, as desired, by heating the disubstituted compound in a mixture of ethanol/water in the presence of a catalyst, such as a rhodium catalyst.

Those compounds of formula I wherein X is

where m is 1 or 2 are readily prepared from the sulfide (i.e., m=0) by treatment with an oxidizing agent, such as m-chloroperbenzoic acid, in an appropriate organic solvent, such as chloroform, for a time sufficient to effect the desired oxidation.

Compounds of formula I wherein $R^3$ is $C_1$–$C_6$ alkyl are prepared by conventional Friedel-Crafts alkylation of the appropriate $R^1,R^2$-substituted phenol, followed by condensation with rhodanine, or the desired N-substituted rhodanine, as described herein or is used as described in the other reaction schemes depicted herein.

It will be readily appreciated by one skilled in the art that the aryl portion of the present compounds of formula I are either commercially available or may be readily prepared by known techniques from commercially available starting materials. For example, p-hydroxybenzaldehyde may be alkylated under Friedel-Crafts conditions to yield an alkylbenzaldehyde which in turn may itself be alkylated. Similarly, the rhodanine or N-substituted rhodanine starting material is either commercially available or may be prepared by well known methodology from commercially available starting materials.

Those compounds of formula I wherein, in the definition of $R^8$ Y is cyano, are prepared by treating the non-cyanated analog with the desired halo-substituted aliphatic nitrile. From the cyano derivative, the tetrazolyl is prepared by treatment with tri-N-butyl tin azide in, for example, ethylene glycol dimethyl ether. Other compounds of formula I may be prepared as more fully described below from compounds whose synthesis was described generically, supra.

Depending upon the definitions of $R^3$, $R^4$ and $R^5$, the compounds of formula I may exist in various isomeric forms. This invention is not related to any particular isomer but includes all possible individual isomers and racemates. In general, such stereoisomers may be obtained according to procedures well-known in the art. However, for compounds of formula I wherein X is —S—; $R^4$ and $R^5$ are hydrogen; and $R^1$, $R^2$, $R^3$, $R^6$, $R^7$ and Q are as defined above, the individual stereoisomers may be isolated in substantially pure isomeric form according to the procedure described in U.S. Pat. No. 5,216,002. The teaching of such application with respect to the stereoisomer isolation process is herein incorporated by reference.

Pharmaceutically acceptable salts of the compounds of formula I are also considered to be encompassed within the method of the present invention. Such salts, which are well-known in the art, may be prepared by reacting a compound of formula I with a strong base, such as sodium hydroxide, or a strong acid such as hydrochloric acid.

The following examples further illustrate the preparation of compounds which may be employed in the method of treating multiple sclerosis provided by this invention. The examples are illustrative only and are not intended to limit the scope of the invention in any way.

EXAMPLE 1

5-[[3,5-bis(1,1-dimethylethyl)-4-hydroxyphenyl] methylene]-2-thioxo-4-thiazolidinone (Compound A)

Under a nitrogen atmosphere, 117.2 g of 3,5-di-tert-butyl-4-hydroxybenzaldehyde, 66.6 g of rhodanine, and 143.5 g of fused sodium acetate were heated at reflux in 2500 ml of glacial acetic acid. After heating for 23 hours, the reaction mixture was cooled and poured into a mixture of 1 liter of ethanol and 1 liter of ice with stirring. 500 ml of water were added and, after stirring for 30 minutes, the resulting precipitate was recovered by filtration. The solid was slurried with 500 ml of ethyl acetate and filtered. The precipitate was then dissolved in 3 liters of ethanol, heated to boiling, and water was added until the solution remained cloudy (approximately 450 ml). Upon cooling to room temperature, 99.6 g of the desired title product were recovered by filtration, m.p. approximately 260° C.

Analysis for $C_{18}H_{23}NO_2S_2$: Calculated: C, 61.86; H, 6.63; N, 4.01; Found: C, 62.13; H, 6.55; N, 4.15.

EXAMPLES 2–3

5-[[3,5-bis(1,1-dimethylethyl)-4-hydroxyphenyl] methylene]-4-thiazolidinone (Compound B) and 5-[[3,5-bis (1,1-dimethylethyl)-4-hydroxyphenyl]methyl]-4-thia zolidinone (Compound C)

A solution of 69.90 g of 5-[[3,5-bis(1,1-(dimethylethyl) - 4-hydroxyphenyl]methylene]-2-thioxo-4-thiazolidinone in 4 liters of ethanol was hydrogenated at 500 pounds per square inch (psi) in the presence of 200 g of 5% palladium on carbon overnight at 100° C. The reaction mixture was filtered and evaporated to dryness. In sections, the material was dissolved in 1 volume of hot ethyl acetate, diluted with 2 volumes of hexane, filtered, and loaded onto a silica gel chromatography column. Elution with 35% ethyl acetate in hexane provided various fractions which were combined according to the purities of the respective compounds. A total of 4.6 g of Compound B were isolated by chromatography. Fractions which were predominantly Compound B were crystallized from ethyl acetate/hexane providing a total yield of Compound B of 13.79 g. Rechromatography of fractions containing impure Compound C on silica eluting with 25% ethyl acetate in hexane provided 9.82 g of Compound C.

2. 5-[[3,5-bis(1,1-dimethylethyl)-4-hydroxyphenyl] methylene]-4-thiazolidinone, m.p. 209°–213° C.

Analysis for $C_{18}H_{25}NO_2S$: Calculated: C, 67.67; H, 7.89; N, 4.38; Found: C, 67.44; H, 8.11; N, 4.65.

3. 5-[[3,5-bis(1,1-dimethylethyl)-4-hydroxyphenyl] methyl]-4-thiazolidinone, m.p. 149°–152° C.

Analysis for $C_{18}H_{27}NO_2S$: Calculated: C, 67.25; H, 8.47; N, 4.36; Found: C, 67.43; H, 8.44; N, 4.21.

EXAMPLE 4

5-[[3,5-bis(1,1-dimethylethyl)-4-hydroxyphenyl] methylene]-4-oxo-3-thiazolidinecarboxylic acid, methyl ester Under a nitrogen atmosphere, 7.03 g of the compound of Example 2 was dissolved in 330 ml of THF to which was added 581 mg of sodium hydride. The mixture was stirred for 10 minutes after which about 2 g of methyl chloroformate was added and the resulting mixture was stirred for an additional 50 minutes. Water (500 ml) and 7 ml of 1N hydrochloric acid (pH of solution about 3) were added. The resultant mixture was extracted twice with 200 ml portions of ethyl acetate. The organic extracts were combined, stripped to dryness, and crystallized from 15 ml of ethylacetate and 25 ml hexane to render the title compound, m.p. 165°–167.5° C.

Analysis for $C_{20}H_{27}NO_4S$: Calculated: C, 63.63; H, 7.21; N, 3.71; Found: C, 63.76; H, 7.33; N, 3.68.

EXAMPLE 5

5-[[3,5-bis(1,1-dimethylethyl)-4-hydroxyphenyl] methylene]-4-oxo-3-thiazolidineacetamide Under a nitrogen atmosphere, 7.03 g of the compound of Example 2 was dissolved in 330 ml of THF. To this was added 0.581 g of sodium hydride and the mixture was stirred for 10 minutes. Iodoacetamide (4.07 g) was added and the resultant mixture was heated at reflux temperature for one hour and then cooled. The solution was then poured into 500 ml of a mixture of rapidly stirred ice/water. The pH of the mixture was reduced to about pH 3 by the addition of 10 ml of 1N hydrochloric acid. The resultant mixture was extracted with three 200 ml portions of ethyl acetate. The extracts were combined, stripped, and crystallized from a mixture of 120 ml of ethyl acetate and 100 ml hexane to render 2.79 g of the title compound, m.p. 232°–235° C.

Analysis for $C_{20}H_{28}N_2O_3S$: Calculated: C, 63.80; H, 7.50; N, 7.44; Found: C, 63.53; H, 7.67; N, 7.14.

EXAMPLE 6

5-[[3,5-bis(1,1-dimethylethyl)-4-hydroxyphenyl] methylene]-3-[2-(methylthio)ethyl]-4-thiazolidinone 26.7 g of 5-[[3,5-Bis(1,1-dimethylethyl)-4-hydroxyphenyl]methylene-4-thiazolidinone (i.e., the compound of Example 2) was dissolved in 418 ml of DMF to which was added 3.34 g of a 60% sodium hydride dispersion. The resultant mixture was stirred at 100° C. under an argon atmosphere. To this was added 8.33 ml of methylthioethyl chloride and the resulting black solution was stirred at 100° C. for 6 days. The material was allowed to cool to 30° C. after which insoluble material was filtered off. The solid was washed with DMF until its color was gone leaving a white solid which was discarded. The pH of the filtrate and washings was adjusted to 1.5 by the addition of 1N hydrochloric acid with stirring. The mixture was then diluted with a mixture of 1000 ml of diethyl ether and 500 ml of 1N hydrochloric acid which was then shaken and separated. The organic layer was washed with two portions of water and one portion of brine and subsequently dried over sodium sulfate, filtered, evaporated and chased with chloroform to give a black foam/oil. This material was triturated with about 75 ml of chloroform and then filtered and the insoluble solid was washed with additional chloroform until its brown color was gone. The filtrate was then loaded onto a silica gel column which was eluted with 8000 ml of a gradient of 10–30% ethyl acetate in hexane. The various fractions containing the desired product were combined and again loaded onto a silica gel column and eluted with 8000 ml of a gradient of 10–35% acetone in hexane. The fractions containing the desired product were recrystalled with hexane/ethyl acetate to give 1.2 g of the title compound as a tan/orange solid, m.p. 165.5°–168° C.

Analysis for $C_{21}H_{31}NO_2S_2$: Calculated: C, 64.08; H, 7.94; N, 3.56; Found: C, 63.99; H, 8.13; N, 3.45.

EXAMPLE 7

5-[[3,5-bis (1,1-dimethylethyl)-4-hydroxyphenyl] methylene]-3-(2-methoxyethyl)-4-thiazolidinone Under an argon atmosphere, 9.58 g of the compound of Example 2 was dissolved in THF with stirring. To this was added 1.2 g of a 60% sodium hydride dispersion and the reaction mixture was then heated to reflux. 2.82 ml of methoxyethylbromide were then added and the resultant mixture was allowed to stir at reflux for five days. After five days, 0.2 equivalents of potassium iodide were added and the reaction was allowed to continue at reflux temperature for an additional two days. The mixture was then allowed to cool and was diluted with diethyl ether and water. The pH of the mixture was adjusted to pH 2 by the addition of 1N hydrochloric acid with stirring. Organic and aqueous layers formed and were separated and the organic layer was washed with saturated sodium bicarbonate, then brine, and subsequently dried over sodium sulfate, filtered, evaporated and then chased with chloroform. The resultant material was then dissolved in 50 ml of chloroform and a precipitate formed. An additional 25 ml of chloroform was added and the mixture was heated. The resultant solution was filtered, chromatographed on silica gel, and subsequently eluted with 8000 ml of a 10–30% gradient of ethyl acetate in hexane followed by elution with 4000 ml of a 30–40% gradient of ethyl acetate in hexane. The various fractions containing the desired product were combined, evaporated to dryness and then chased with chloroform to render an orange sticky solid. This material was then dissolved in 15 ml of ethyl acetate with heating on a steam bath and subsequently diluted with 250 ml of hexane. The mixture was allowed to cool to room temperature, with precipitate forming, and allowed to stand for three days. The material was filtered and washed with hexane to yield 5.16 g of the title compound, m.p. 147°–149° C.

Analysis for $C_{21}H_{31}NO_3S$: Calculated: C, 66.80; H, 8.28; N, 3.71; Found: C, 67.04; H, 8.30; N, 3.74.

EXAMPLE 8

5-[[3,5-bis(1,1-dimethylethyl)-4-hydroxyphenyl]methyl] -2-thioxo-4-thiazolidinone (Compound D)

Under a nitrogen atmosphere, 13.98 g of 5-[[3,5-bis(1,1-dimethylethyl)-4-hydroxyphenyl]methylene]-2-thioxo-4-thiazolidinone, 13.17 g of diethyl 2,6-dimethyl-1,4-dihydro-3,5-pyridinedicarboxylate and 600 ml of toluene were stirred to effect solution. Forty grams of silica gel 60 (finer than 230 mesh) previously dried in vacuo at 50° C. for 7 hours were added to the reaction. The reaction was heated at reflux for 18 hours and filtered hot. The filtrate was evaporated to dryness. The residue was dissolved in 500 ml of ethyl acetate, washed 5 times each with 400 ml of 1N hydrochloric acid, dried over sodium sulfate, filtered, and evaporated in vacuo to provide a yellow solid. Chromatography over silica gel eluting with 2.5% ethyl acetate in toluene provided 8.0 g of the desired title product, m.p. 178°–179° C.

Analysis for $C_{18}H_{25}NO_2S_2$: Calculated: C, 61.50; H, 7.17; N, 3.98; Found: C, 61.28; H, 7.19; N, 3.94.

EXAMPLE 9

5-[[3,5-bis(1,1-dimethylethyl)-4-hydroxyphenyl] methylene]-3-methyl -2-thioxo -4-thiazolidinone The title compound was prepared in 76% yield from 3,5-di-tert-butyl-4-hydroxybenzaldehyde and N-methylrhodanine following the procedure of Example 1, m.p. >230° C.

Analysis for $C_{19}H_{25}NO_2S_2$: Calculated: C, 62.77; H, 6.93; N, 3.85; S, 17.64; Found: C, 62.54; H, 7.05; N, 3.66; S, 17.82.

EXAMPLE 10

5-[[3,5-bis(1,1-dimethylethyl)-4-hydroxyphenyl] methylene]-3-methyl-4-thiazolidinone The title compound was prepared in 71% yield from 10.31 g of the thione of Example 9 upon heating with 38.15 ml of tri-n-butyl tin hydride and 1.16 g of azobisisobutyronitrile (AIBN) in 142 ml of toluene at reflux temperature for one hour. The product was isolated by adding water to the cooled reaction mixture, separating the layers, washing the organic layer with 1N hydrochloric acid and a saturated sodium chloride solution, drying over magnesium sulfate, concentrating in vacuo, and purifying the residue by chromatography over silica gel eluting with a 10–50% hexane in ethyl acetate gradient. The purified product had a melting point of 142°–144° C.

Analysis for $C_{19}H_{27}NO_2S$: Calculated: C, 68.43; H, 8.16; N, 4.20; Found: C, 68.68; H, 8.00; N, 3.97.

EXAMPLE 11

5-[[3,5-bis(1,1-dimethylethyl)-4-hydroxyphenyl]methyl] -3-methyl-4-thiazolidinone To 100 ml of THF was added 6.43 g of the compound of Example 3. Sodium hydride (0.9 g) was added, resulting in the evolution of a gas. 1.25 ml (1.0 eq.) of iodomethane was added and the resultant mixture was stirred at room temperature for 23 hours after which the mixture was diluted with a volume of diethyl ether and 1N HCl. The organic layer was separated and dried over sodium sulfate, filtered and evaporated. The resultant solid was chased with chloroform to render an orange foam. A 5.93 g sample of this material was dissolved in 14 ml of a hot mixture of ethyl acetate diluted with 225 ml of hexane and then allowed to cool to room temperature overnight. The solvent was evaporated and the resultant solid was dissolved in 40 ml of a hot mixture of diethyl ether diluted with about 400 ml of hexane. The mixture was allowed to cool to room temperature overnight and a precipitate formed which was collected by filtration, washed with hexane and dried in vacuo to render 3.98 g of the desired, title compound, m.p. 102°–105° C.

Analysis for $C_{19}H_{29}NO_2S$: Calculated: C, 68.02; H, 8.71; N, 4.17; Found: C, 68.22; H, 8.80; N, 4.21.

EXAMPLE 12

5-[[3,5-bis (1,1-dimethylethyl)-4-hydroxyphenyl] methylene]-3-methyl-4-thiazolidinone, 1-oxide Under a nitrogen atmosphere, 6.67 g of the compound of Example 10 was dissolved in 100 ml of chloroform with stirring and the resultant mixture was cooled to 4° C. Meta-chloroperbenzoic acid was added dropwise (with additional chloroform) after which the reaction mixture was poured into a separatory funnel and washed with saturated sodium bicarbonate. The layers were separated, and the organic layer was dried over sodium sulfate, filtered and evaporated to give a white foam. The foam was dissolved in 70 ml of ethyl acetate with heating on a steam bath and diluted with 125 ml of hexane while boiling. A precipitate formed and the reaction mixture was allowed to cool to room temperature overnight. The precipitate was filtered, subsequently washed with hexane, and dried under vacuum at room temperature for two hours to render 6.10 g of the title compound, m.p. 183°–184° C.

Analysis for $C_{19}H_{27}NO_3S$: Calculated: C, 65.30; H, 7.79; N, 4.01; Found: C, 65.46; H, 7.68; N, 4.01.

EXAMPLE 13

5-[[3,5-bis(1,1-dimethylethyl)-4-hydroxyphenyl] methylene]-3-methyl-4-thiazolidinone, 1,1-dioxide Under a nitrogen atmosphere, 1 g of the compound of Example 10 was dissolved in 15 ml of chloroform with stirring while cooled in an ice bath. To this was added, dropwise, 1.29 g of m-chloroperbenzoic acid and an additional 18 ml of chloroform such that the addition was complete in 15 minutes. The mixture was removed from the ice bath, stirred at room temperature for 22 hours, transferred to a separatory funnel and then washed with a saturated sodium bicarbonate solution. The layers were separated and the organic layer was washed with brine, separated, dried over sodium sulfate, filtered and evaporated. The resultant residue was taken up in 12 ml of ethyl acetate and diluted with 50 ml of hexane while boiling on a steam bath. The mixture was allowed to cool to room temperature overnight and the resultant precipitate was filtered, washed with hexane and dried in vacuo to yield 0.75 g of the desired titled compound, m.p. 217°–221° C.

Analysis for $C_{19}H_{27}NO_4S$: Calculated: C, 62.44; H, 7.45; N, 3.83; Found: C, 62.17; H, 7.26; N, 3.95.

EXAMPLE 14

5-[[3,5-bis(1,1-dimethylethyl)-4-hydroxyphenyl] methylene]-3-ethyl-4-thiazolidinone To a solution of 9.58 g of 5-[[3,5-bis(1,1-dimethylethyl)-4-hydroxyphenyl]methylene]-4-thiazolidinone in 150 ml of tetrahydrofuran were added 1.20 g of a 60% dispersion of sodium hydride in mineral oil. After gas evolution ceased, 2.4 ml of ethyl iodide were added and the reaction mixture was stirred for two days under an argon atmosphere. The mixture was heated at reflux for six hours, cooled, diluted with diethyl ether and water, and adjusted to pH 3 with 1N hydrochloric acid. The layers were separated, and the organic layer was washed with a saturated sodium bicarbonate solution followed by a saturated sodium chloride solution. Concentration of the dried organic solution and chromatography of the resulting residue over silica gel eluting with a 10–30% ethyl acetate in hexane gradient provided 3.65 g of the desired title product, m.p. 169°–172.5° C.

Analysis for $C_{20}H_{29}NO_2S$: Calculated: C, 69.12; H, 8.41; N, 4.03; Found: C, 69.39; H, 8.52; N, 4.30.

EXAMPLES 15–16

The following compounds were prepared from the appropriate alkyl iodide according to the procedure of Example 14.

15. 5-[[3,5-bis(1,1-dimethylethyl)-4-hydroxyphenyl] methylene]-3-propyl-4-thiazolidinone, 60% yield, m.p. 145°–146.5° C.

Analysis for $C_{21}H_{31}NO_2S$: Calculated: C, 69.76; H, 8.64; N, 3.87; Found: C, 70.05; H, 8.76; N, 4.01.

16. 5-[[3,5-bis(1,1-dimethylethyl)-4-hydroxyphenyl] methylene]-3-butyl-4-thiazolidinone, 60% yield, m.p. 168.5°–169.5° C.

Analysis for $C_{22}H_{33}NO_2S$: Calculated: C, 70.36; H, 8.86; N, 3.73; Found: C, 70.60; H, 8.81; N, 3.97.

EXAMPLES 17–19

The following compounds were prepared according to the procedure of Example 1 (or as set forth elsewhere herein) employing an appropriate N-substituted rhodanine and benzaldehyde.

17. 5-[[3-methylthiophenyl)-4-hydroxy-5-ethoxyphenyl]methylene]-2-thioxo-3-methyl-4-thiazolidinone, m.p. 137° C.

Analysis for $C_{20}H_{19}NO_3S_3$: Calculated: C, 57.53; H, 4.59; N, 3.35; Found: C, 58.80; H, 4.38; N, 3.43.

18. 5-[[3,5-bis(1,1-dimethylethyl)-4-hydroxyphenyl] methylene]-3-cyclopropyl-2-thioxo-4-thiazolidinone, 93% yield, m.p. 158°–168° C.

19. 5-[[3,5-bis(1,1-dimethylethyl)-4-hydroxyphenyl] methylene]-3-dimethylamino-2-thioxo-4-thiazolidinone, 65% yield.

EXAMPLES 20–21

The thiones of Examples 18–19 were reduced using the procedure of Example 10 to provide the following compounds of the invention.

20. 5-[[3,5-bis(1,1-dimethylethyl)-4-hydroxyphenyl] methylene]-3-cyclopropyl-4-thiazolidinone, 46% yield, m.p. 162°–164° C.

Analysis for $C_{21}H_{29}NO_2S$: Calculated: C, 70.16; H, 8.13; N, 3.90; Found: C, 69.91; H, 8.23; N, 3.75.

21. 5-[[3,5-bis(1,1-dimethylethyl)-4-hydroxyphenyl] methylene]-3-(dimethylamino)-4-thiazolidinone, 41% yield, m.p. 138°–141° C.

Analysis for $C_{20}H_{30}N_2O_2S$: Calculated: C, 66.26; H, 8.34; N, 7.73; Found: C, 66.55; H, 8.59; N, 7.47.

EXAMPLE 22

5-[[3,5-bis(1,1-dimethylethyl)-4-hydroxyphenyl] methylene]-3-(dimethylamino)-4-thiazolidinone, 1-oxide Under a nitrogen atmosphere, 9.06 g of the compound of Example 21 was dissolved in 125 ml of chloroform with stirring while cooled in an ice bath. To this was added (dropwise) 5.39 g of meta-chloroperbenzoic acid in 75 ml of chloroform over a period of 25 minutes at 0° C. After an additional 10 minutes, the reaction mixture was transferred to a separatory funnel, washed with saturated sodium bicarbonate and the layers separated. The aqueous layer was washed with chloroform. This wash was added to the original chloroform extract resulting in a slow breaking emulsion. The organic layer was dried over sodium sulfate, filtered, washed and the solvent removed by evaporation. The resultant residue was subsequently taken up in about 225 ml of ethyl acetate with heating on a steam bath and then diluted with about 100 ml of hexane. A precipitate formed and the resultant mixture was allowed to cool to room temperature overnight. The precipitate was filtered, washed with hexane, allowed to air dry for one hour and subsequently dissolved in 100 ml of isopropyl alcohol on a steam bath. The resultant solution was allowed to cool to room temperature overnight resulting in a precipitate which was again washed with hexane and dried under vacuum at 80° C. for about four hours to yield 5.41 g of the title compound, m.p. 198°–201° C.

Analysis for $C_{20}H_{30}N_2O_3S$: Calculated: C, 63.46; H, 7.97; N, 7.40; Found: C, 63.68; H, 7.78; N, 7.56.

EXAMPLE 23

5-[[3,5-bis(1,1-dimethylethyl)-4-hydroxyphenyl]methylene]-4-thiazolidinone, 1-oxide Utilizing the procedures set forth in Example 22, 5.12 g of the title compound was prepared from 5-[[3,5-bis(1,1-dimethylethyl)-4-hydroxyphenyl]methylene]-3-dimethylamino -4-thiazolidinone (i.e., the compound of Example 21), m.p. 103°–110° C.

Analysis for $C_{18}H_{25}NO_3S$: Calculated: C, 63.77; H, 8.41; N, 3.54; Found: C, 64.11; H, 8.26; N, 3.55.

Utilizing the procedures set forth herein the following additional compounds were prepared.

EXAMPLE 24

5-[[3,5-bis(1,1-dimethylethyl)-4-hydroxyphenyl]methylene]-3-(2-propenyl)-4-thiazolidinone, m.p. 154.5°–156.5° C.

Analysis for $C_{21}H_{29}NO_2S$: Calculated: C, 70.16; H, 8.13; N, 3.90; S, 8.92; Found: C, 70.27; H, 8.21; N, 4.01; S, 9.09.

EXAMPLE 25

5-[[3,5-bis(1,1-dimethylethyl)-4-hydroxyphenyl]methylmethylene]-3-methyl-4-thiazolidinone, m.p., 152.5°–153.5° C.

Analysis for $C_{20}H_{29}N_2S$: Calculated: C, 69.12; H, 8.41; N, 4.03; Found: C, 69.18; H, 8.25; N, 4.26.

EXAMPLE 26

5-[[3,5-bis(1,1-dimethylethyl)-4-hydroxyphenyl]methylene]-3-[2-(acetyloxy)ethyl]-4-thiazolidinone A. Preparation of N-(2-hydroxyethyl)rhodanine Sixty milliliters of carbon disulfide were added to 200 ml of diethyl ether. The solution was chilled to –5° C. and slowly added to a solution of 138 ml of ethanolamine in 250 ml of ethanol. After holding the mixture at ambient temperature for 16 hours, the resulting top layer was decanted and the residual oil washed twice with 50 ml of diethyl ether. To the oil was added a solution of 71 g of chloroacetic acid in 150 ml of 5N sodium hydroxide at 0° C. The cooling bath was removed and the reaction was allowed to stand for 75 minutes. The mixture was poured into 400 ml of 6N hydrochloric acid and the resulting mixture heated to 91° C. for 20 minutes. The heat was removed, and the solution allowed to stand for 5 hours at ambient temperature. An oily organic layer was separated from the aqueous layer and the aqueous layer extracted twice with 250 ml of ethyl acetate. The organic layers were combined, washed twice with a saturated sodium chloride solution, dried and concentrated in vacuo to provide 113.4 g of the desired subtitled intermediate, which was used without further purification.

B. Preparation of 5-[[3,5-bis(1,1-dimethylethyl)-4-hydroxyphenyl]methylene]-3-[2-(acetyloxy)ethyl]-2-thioxo-4-thiazolidinone A mixture of 124 g of 3,5-di-tert-butyl-4-hydroxybenzaldehyde, 103.1 g of the subtitle intermediate of Example 26A above, 346.9 g of sodium acetate, and 2.65l of glacial acetic acid was heated at reflux temperature for 7.5 hours under a nitrogen atmosphere. The heat was removed and the mixture allowed to cool overnight with stirring. The resulting precipitate was removed by filtration and the filtrate concentrated in vacuo. Two liters of ethyl acetate were added to the residue followed by 1.5l of water. The layers were separated and the water layer extracted with 500 ml of ethyl acetate. The organic layers were combined, washed with water and a sodium bicarbonate solution, dried over sodium sulfate, and concentrated in vacuo. The residue was purified by chromatography over silica gel, eluting with a gradient of toluene to 7% ethyl acetate in toluene. The appropriate fractions were combined and concentrated in vacuo. The residue was crystallized from 75 ml of ethanol to provide 10.28 g of the desired subtitled intermediate, m.p. 140°–143° C.

C. 5-[[3,5-bis(1,1-dimethylethyl)-4-hydroxyphenyl]methylene]-3-[2-(acetyloxy)ethyl]-4-thiazolidinone Under a nitrogen atmosphere, 82.2 g of 5-[[3,5-bis(1,1-dimethylethyl)-4-hydroxyphenyl]methylene]-3-[2-(acetyloxy) ethyl]-2-thioxo-4-thiazolidinone in 950 ml of toluene was heated to 65° C. Tri-n-butyl tin hydride (219.7 g) and AIBN (4.65 g) were added and the solution heated at reflux temperature for an additional 10 minutes. After cooling, the mixture was washed with 1.25l of 1N hydrochloric acid followed by 500 ml of a saturated sodium chloride solution. The organic layer was stripped and allowed to stand overnight, during which time a precipitate separated. The liquid portion was decanted off, and the resulting residue was purified by chromatography over silica gel, eluting with a gradient of 25–50% of ethyl acetate in hexane. The appropriate fractions were combined and concentrated in vacuo to provide 45.7 g of the desired titled compound, m.p.=152°–155° C.

Analysis for $C_{22}H_{31}NO_4S$: Calculated: C, 60.66; H, 6.71; N, 3.22; Found: C, 60.71; H, 6.90; N, 3.21.

EXAMPLE 27

5-[[3,5-bis(1,1-dimethylethyl)-4-hydroxyphenyl]methylene]-3-(2-aminoethyl)-4-thiazolidinone A. Preparation of 5-[[3,5-bis(1,1-dimethylethyl)-4-hydroxyphenyl]methylene]-3-(2-hydroxyethyl)-4-thiazolidinone A solution of 85.2 g of 5-[[3,5-bis(1,1-dimethylethyl)-4-hydroxyphenyl]methylene]-3-[2-(acetyloxy)ethyl]-4-thiazolidinone from Example 26 in 1.5 l of acetonitrile was treated with 1 liter of concentrated ammonium hydroxide. The reaction mixture was allowed to stand for approximately 90 hours at room temperature. The solution was concentrated in vacuo and 500 ml of ethyl acetate were added, with the pH adjusted to 3.0 with concentrated hydrochloric acid. The layers were separated and the aqueous layer extracted with 250 ml of ethyl acetate. The combined organic layers were washed with 250 ml of a saturated sodium chloride solution and concentrated in vacuo. The residue was crystallized from 95 ml of hexane and 70 ml of ethyl acetate to provide 35.68 g of the desired subtitled intermediate, m.p. 131°–135° C.

Analysis for $C_{20}H_{29}NO_3S$: Calculated: C, 66.08; H, 8.04; N, 3.85; Found: C, 65.91; H, 8.21; N, 3.96.

B. Preparation of 5-[[3,5-bis(1,1-dimethylethyl)-4-hydroxyphenyl]methylene]-3-[2-(tosyloxy)ethyl]-4-thiazolidinone A solution of 30.2 g of the hydroxyethyl intermediate of Example 27A, above, in 415 ml of pyridine was cooled to −3° C. and 39.6 g of p-toluenesulfonyl chloride was added with stirring. After stirring the mixture at 0° C. for 4 hours, the solution was stored in a refrigerator overnight at −10° C. Approximately 1 liter of ice water was added and the mixture extracted twice with 700 ml of diethyl ether. The combined organic layers were washed twice with 1 liter of 1N hydrochloric acid and ice, dried over sodium sulfate and concentrated in vacuo to provide 41.7 g of the desired tosyl intermediate, which was used without further purification.

C. Preparation of 5-[[3,5-bis(1,1-dimethylethyl)-4-hydroxyphenyl]methylene]-3-(2-aminoethyl)-4-thiazolidinone A mixture of 13 g of the tosyl intermediate of Example 27B, above, 250 ml of concentrated ammonium hydroxide, and 250 ml of acetonitrile was stirred for 2 days at room temperature. The mixture was concentrated in vacuo and diluted with 500 ml of ethyl acetate. The pH was adjusted to 9.0 and the layers separated. The organic layer was washed twice with water, dried, and concentrated in vacuo. The residue was purified by chromatography over silica gel, eluting with a gradient from methylene chloride to 90:10:1 methylene chloride/ethanol/ammonium hydroxide, respectively. The desired fractions were combined and concentrated in vacuo. The residue was triturated with hexane to provide 1.47 g of the desired title product, m.p. 176°–178° C.

Analysis for $C_{20}H_{30}N_2O_2S$: Calculated: C, 66.26; H, 8.32; N, 7.73; Found: C, 66.25; H, 8.24; N, 7.59.

EXAMPLES 28–30

The following compounds were prepared by reacting the intermediate of Example 27B with the appropriate amine according to the procedures described herein.

28. 5-[[3,5-bis(1,1-dimethylethyl)-4-hydroxyphenyl]methylene]-3-[2-(methylamino)ethyl]-4-thiazolidinone, 28% yield, m.p. 137°–140° C.

Analysis for $C_{21}H_{32}N_2O_2S$: Calculated: C, 66.98; H, 8.57; N, 7.44; Found: C, 66.76; H, 8.33; N, 7.24.

29. 5-[[3,5-bis(1,1-dimethylethyl)-4-hydroxyphenyl]methylene]-3-[2-(dimethylamino)ethyl]-4-thiazolidinone, 64% yield, m.p. 148°–153° C.

Analysis for $C_{22}H_{34}N_2O_2S$: Calculated: C, 67.65; H, 8.77; N, 7.17; Found: C, 67.43; H, 8.55; N, 6.98.

30. 5-[[3,5-bis(1,1-dimethylethyl)-4-hydroxyphenyl]methylene]-3-[2-(2-hydroxyethylamino)ethyl]-4-thiazolidinone, 59% yield, m.p. 174°–176° C.

Utilizing the procedures set forth herein the following additional compounds were prepared.

EXAMPLE 31

5-[[3,5-bis(1,1-dimethylethyl)-4-hydroxyphenyl]methylene]-3-[2-(methyl-2-propynylamino)ethyl]-4-thiazolidinone, m.p. 116°–118° C.

Analysis for $C_{24}H_{34}N_2O_2S$: Calculated: C, 69.53; H, 8.27; N, 6.76; Found: C, 69.27; H, 8.46; N, 6.65.

EXAMPLE 32

5-[[3,5-bis(1,1-dimethylethyl)-4-hydroxyphenyl]methylene]-3-[2-[[2-(dimethylamino)ethyl]amino]ethyl]-4-thiazolidinone, m.p. 245°–249° C. (dec.)

Analysis for $C_{24}H_{39}N_3O_2S$: Calculated: C, 56.90; H, 8.16; N, 8.30; Found: C, 57.12; H, 7.98; N, 8.09.

EXAMPLE 33

5-[[3,5-bis(1,1-dimethylethyl)-4-hydroxyphenyl]methylene]-3-[2-[(phenylmethyl)amino]ethyl]-4-thiazolidinone hydrochloride, m.p. 254°–259° C. (dec.)

Analysis for $C_{27}H_{36}N_2O_2S$: Calculated: C, 66.30; H, 7.63; N, 5.73; Found: C, 66.46; H, 7.53; N, 5.80.

EXAMPLE 34

5-[[3,5-bis(1,1-dimethylethyl)-4-hydroxyphenyl]methylene]-3-[3-(methylamino)propyl]-4-thiazolidinone, m.p. 177°–180° C.

Analysis for $C_{22}H_{34}N_2O_2S$: Calculated: C, 67.65; H, 8.77; N, 7.17; Found: C, 67.72; H, 8.94; N, 7.00.

EXAMPLE 35

5-[[3,5-bis(1,1-dimethylethyl)-4-hydroxyphenyl]methylene]-3-(2-hydroxyethyl)-4-thiazolidinone, m.p. 131°–135° C.

Analysis for $C_{20}H_{29}NO_3S$: Calculated: C, 66.08; H, 8.04; N, 3.85; Found: C, 66.36; H, 8.13; N, 3.87.

EXAMPLE 36

5-[[3,5-bis(1,1-dimethylethyl)-4-hydroxyphenyl]methylene]-3-[(4-methoxyphenyl)methyl]-4-thiazolidinone, m.p. 129°–130° C.

Analysis for $C_{26}H_{33}N_3S$: Calculated: C, 71.04; H, 7.57; N, 3.19; Found: C, 70.75; H, 7.69; N, 3.18.

EXAMPLE 37

5-[[3,5-bis(1,1-dimethylethyl)-4-hydroxyphenyl]methylene]-3-[2-(propylamino)ethyl]-4-thiazolidinone, m.p. 155°–158° C.

Analysis for $C_{23}H_{36}N_2O_2S$: Calculated: C, 68.28; H, 8.97; N, 6.92; Found: C, 68.38; H, 9.17; N, 7.13.

EXAMPLE 38

5-[[3,5-bis(1,1-dimethylethyl)-4-hydroxyphenyl]methylene]-4-oxo-3-thiazolidineacetonitrile.

7.03 g of 5-[[3,5-Bis(1,1-dimethylethyl)-4-hydroxyphenyl]methylene]-4-thiazolidinone and 2.64 g of bromoacetonitrile were reacted in the presence of 0.97 g of 60% sodium hydride in mineral oil and 330 ml of tetrahydrofuran. Work-up of the reaction mixture provided 3.21 g of the desired title product, m.p. 186°–188° C.

Analysis for $C_{20}H_{26}N_2O_2S$: Calculated: C, 67.01; H, 7.31; N, 7.81; Found: C, 66.80; H, 7.36; N, 7.67.

EXAMPLE 39

5-[[3,5-bis(1,1-dimethylethyl)-4-hydroxyphenyl]methylene]-3-(1H-tetrazol-5-ylmethyl)-4-thiazolidinone The title compound was prepared from the nitrile of Example 38 by treatment with tri-N-butyl azide in ethylene glycol dimethyl ether, melting point 260°–263° C. (dec.)

Analysis for $C_{20}H_{27}N_5O_2S$: Calculated: C, 59.83; H, 6.78; N, 17.44; Found: C, 59.93; H, 6.82; N, 17.32.

EXAMPLE 40

5-[[3,5-bis(1,1-dimethylethyl)-4-hydroxyphenyl]methylene]-3-(ethylmethylamino)-4-thiazolidinone A. Preparation of nitrosomethylethylamine 70.15 g of methylethylamine was maintained at 10° C. on an ice bath. To this was added 104 ml of concentrated hydrochloric acid (dropwise with stirring). The addition of the hydrochloric acid was continued at a rate which maintained the reaction temperature at about 15° C. Upon completion of the acid addition, 90 g of sodium nitrite was added to the reaction in small portions. Upon dissolution of the sodium nitrite, a gas formed and the temperature of the reaction mixture dropped to about 0° C. The mixture was placed in an oil bath and heated to about 70° C. during completion of the sodium nitrite addition. After about 90 minutes, gas evolution had ceased and an additional 10 ml of concentrated hydrochloric acid was added generating additional gas evolution. Upon further stirring, an additional 5 ml of concentrated hydrochloric acid was added. The reaction mixture was allowed to stir overnight, with cooling, after which the resultant layers were separated. The upper layer was extracted with a 100 ml portion of diethyl ether followed by a second extraction with an additional 50 ml of diethyl ether. The extracts were combined and evaporated on a steam bath to yield 26.8 g of the desired subtitled intermediate.

B. Preparation of N,N-methylethylhydrazine

To a stirred mixture of 46.75 g nitrosomethylethylamine, 588 ml of water and 133.9 g of zinc dust was added (dropwise) 159 ml of acetic acid. The addition was completed over approximately two hours, and the reaction mixture was maintained at 25°–30° C. The reaction mixture was then heated to about 90° C., allowed to cool after about 30 minutes to 60° C., allowed to cool to room temperature and then filtered. The aqueous filtrate was then cooled in an ice bath and adjusted to pH 11 with 50% sodium hydroxide. A white precipitate formed which made additional stirring difficult. The white suspension was filtered and washed with two portions of water. The original filtrate and the first wash were combined for distillation. The mixture was heated and various fractions collected over a temperature range of about 67° C. to 99° C., each of which contained the desired subtitled intermediate.

C. Preparation of S-carboxymethyl-N'-dithiocarboxy N-methyl-N-ethylhydrazine

N,N-Methylethylhydrazine (13.3 g) and 20 ml of ethanol were cooled in an ice/water bath. To this was added a mixture of 4.69 ml of carbon disulfide and 15.6 ml of diethyl ether, dropwise, with stirring over a period of about 13 minutes. The resultant yellow solution was stirred for an additional 15 minutes at 0° C. and then removed from the ice bath. Additional diethyl ether was added to induce the formation of a precipitate. When the total volume reached 125 ml (due to addition of diethyl ether) two layers had formed. Within about 10 minutes the oily lower layer began to crystallize and the reaction mixture was allowed to stand at room temperature overnight. The reaction mixture was then maintained at 5° C. for two hours prior to filtering. The mixture was filtered, washed with diethyl ether, dried under vacuum at room temperature for three hours and then added to a stirred, cooled (4° C.) mixture of 5.66 g of chloroacetic acid in 12 ml of 5N sodium hydroxide. The reaction mixture was then removed from the ice bath, allowed to warm to room temperature with stirring for 45 minutes, and then added over a period of about 2 minutes to 31.2 ml of 6N hydrochloric acid heated to 85° C. The mixture was warmed to 90° C. over approximately 10 minutes and allowed to cool while stirring to room temperature overnight. A precipitate formed which was filtered, washed lightly with cold water and allowed to air dry for about 15 minutes. The precipitate was then dried under vacuum at 80° C. for three days to yield 4.64 g of the desired subtitled intermediate. The filtrate was stirred at room temperature for 3 days and additional precipitate formed which was subsequently filtered, washed lightly with water and dried under vacuum at 80° C. for 24 hours to yield an additional 1.76 g of the desired subtitled intermediate.

D. Preparation of 5-[[3,5-bis(1,1-dimethylethyl)-4-hydroxyphenyl]methylene]-3-(ethylmethylamino)-2-thioxo-4-thiazolidinone Under nitrogen atmosphere, 6.40 g of the intermediate prepared in Example 40C, 154 ml of acetic acid and 8.82 g of sodium acetate were stirred for 10 minutes. 7.2 g of 3,5-bis(1,1-dimethylethyl)-4-hydroxybenzaldehyde was added and the resultant mixture was heated at reflux temperature for 23 hours and poured into a 400 ml mixture of ice/water with stirring. The resultant mixture was stirred for an additional 20 minutes, filtered and washed with a volume of water to give the desired subtitled intermediate. This intermediate was dried under vacuum at 100° C. for three days, after which it was dissolved in 45 ml of ethanol on a steam bath and diluted with water dropwise while stirring until cloudiness persisted. This mixture was then stirred for an additional five minutes, allowed to cool to room temperature overnight and dried under vacuum at 80° C. for four hours to render 6.99 g of the desired subtitled intermediate.

E. Preparation of 5-[[3,5-bis(1,1-dimethylethyl)-4-hydroxyphenyl]methylene]-3-(ethylmethylamino)-4-thiazolidinone 7.02 g of 5-[[3,5-bis(1,1-dimethylethyl)-4-hydroxyphenyl]methylene]-3-(ethylmethylamino)-2-thioxo-4-thiazolidinone (from Example 40D) and 86.3 ml of toluene were stirred and heated to 60° C. under a nitrogen atmosphere. To this was added 18.6 ml of tri-n-butyl tin hydride and 0.43 g of AIBN. The resultant mixture was heated to reflux temperature for 30 minutes. At that time an additional 0.43 g of AIBN was added. The resultant mixture was heated at reflux temperature for an additional 30 minutes, cooled and transferred to a separatory funnel. To this was added 100 ml of 1N hydrochloric acid and 100 ml of ethyl acetate. The resultant mixture was shaken and separated. The organic layer was washed with brine, dried over sodium sulfate, filtered, evaporated and subsequently chased with chloroform to give an orange/red oil which was taken up in 50 ml of chloroform and filtered. The filtrate was chromatographed on a silica gel column using an 8000 ml gradient of 10–40% ethyl acetate in hexane. Those fractions identified as containing product were evaporated and chased with chloroform. To these fractions were added 15 ml of hexane and the resultant solution was heated slightly. A precipitate formed which was diluted to about 25 ml with additional hexane. The resultant mixture was triturated for about 2 hours, filtered and then washed with hexane to yield 1.94 g of the desired product, m.p. 133.5°–135° C.

Analysis for $C_{21}H_{32}N_2O_2S$: Calculated: C, 66.98; H, 8.57; N, 7.44; Found: C, 66.97; H, 8.80; N, 7.24.

Utilizing the procedures substantially as described in Example 40 and described elsewhere herein, the following additional compounds were prepared.

EXAMPLE 41

5-[[3,5-bis(1,1-dimethylethyl)-4-hydroxyphenyl] methylene]-3-(butylmethylamino)-4-thiazolidinone, m.p. 128.5°–131° C.

Analysis for $C_{23}H_{36}N_2O_2S$: Calculated: C, 68.28; H, 8.97; N, 6.92; Found: C, 68.45; H, 9.00; N, 6.70.

EXAMPLE 42

5-[[3,5-bis(1,1-dimethylethyl)-4-hydroxyphenyl] methylene]-3-[(2-phenylethyl)methylamino]-4-thiazolidinone, m.p. 93°–97° C.

Analysis for $C_{27}H_{36}N_2O_2S$: Calculated: C, 71.64; H, 8.02; N, 6.19; Found: C, 71.48; H, 8.30; N, 5.81.

EXAMPLE 43

5-[[3,5-bis(1,1-dimethylethyl)-4-hydroxyphenyl] methylene]-3-(4-methyl-1-piperazinyl)-4-thiazolidinone, m.p. 221°–225° C.

Analysis for $C_{23}H_{34}N_2O_2S$: Calculated: C, 66.15; H, 8.45; N, 10.06; Found: C, 66.10; H, 8.36; N, 9.81.

EXAMPLE 44

5-[[3,5-bis(1,1-dimethylethyl)-4-hydroxyphenyl] methylene]-3-(1-piperidinyl)-4-thiazolidinone, m.p. 213°–215° C.

Analysis for $C_{23}H_{34}N_2O_2S$: Calculated: C, 68.62; H, 8.51; N, 6.96; Found: C, 68.41; H, 8.49; N, 7.26.

EXAMPLE 45

5-[[3,5-bis(1,1-dimethylethyl)-4-hydroxyphenyl] methylene]-3-(4-morpholinyl)-4-thiazolidinone, m.p. 226°–228° C.

Analysis for $C_{22}H_{32}N_2O_3S$: Calculated: C, 65.31; H, 7.97; N, 6.92; Found: C, 65.59; H, 7.94; N, 7.20.

EXAMPLE 46

5-[[3,5-bis(1,1-dimethylethyl)-4-hydroxyphenyl] methylmethylene]-3-(dimethylamino)-4-thiazolidinone A. Preparation of 1-[3,5-bis(1,1-dimethylethyl)-4-hydroxyphenyl]ethanone Under a nitrogen atmosphere, 6.89 ml of acetylchloride and 14.75 ml of stannic chloride were dissolved in 200 ml of methylene chloride and chilled to −4° C. To this was added 20 g of 2,6-di-t-butylphenol (in 100 ml of methylene chloride) over 10 minutes. The resultant mixture was stirred for 30 minutes at 0° C., then poured into a mixture of 400 ml of ice and 1N hydrochloric acid and stirred. The mixture separated into layers which were subsequently separated. The organic layer was washed with 100 ml of saturated sodium bicarbonate and 100 ml of brine. The organic layer was dried and the solvent evaporated to give 23.39 g of the desired subtitled intermediate.

B. Preparation of 5-[[3,5-bis(1,1-dimethylethyl)-4-hydroxyphenyl]methylmethylene]-3-(dimethylamino)-2-thioxo-4-thiazolidinone To 675 ml of toluene were added 20.9 g of 1-[3,5-bis(1,1-dimethylethyl)-4-hydroxyphenyl]ethanone, 13.3 g of N-dimethylaminorhodanine 6.5 g of ammonium acetate and about 20 ml of acetic acid. The mixture was heated at reflux temperature and any aqueous layer generated was collected in a Dean-Stark trap. Over the following 52 hours an additional 39 g of ammonium acetate and about 100 ml of acetic acid were added in increments and a total of 89.2 ml of aqueous phase was drawn off. Following workup by conventional techniques, 17.1 g of the desired subtitled intermediate was recovered.

C. Preparation of 5-[[3,5-bis(1,1-dimethylethyl)-4-hydroxyphenyl]methylmethylene]-3-(dimethylamino)-4-thiazolidinone Utilizing the procedure set forth in Example 40E, reduction of the thione was effected utilizing tri-n-butyl tin hydride and AIBN in toluene to render the desired title compound, m.p. 181°–186° C.

Analysis for $C_{21}H_{32}N_2O_2S$: Calculated: C, 66.98; H, 8.57; N, 7.44; Found: C, 66.84; H, 8.48; N, 7.39.

EXAMPLE 47

5-[[3,5-bis(1,1-dimethylethyl)-4-hydroxyphenyl] methylene]-3-(methylamino)-4-thiazolidinone A. Preparation of benzaldehydemethylhydrazone 50.8 ml of benzaldehyde (500 mmol) and 26.5 ml (500 mmol) of methylhydrazine were dissolved in 1 liter of methanol. The mixture was stirred together at room temperature for 75 minutes and then stripped of solvent to give 67.8 g of the desired subtitled intermediate.

B. Preparation of benzaldehyde N-methyl, N-2-propenylhydrazone 67.8 g of benzaldehydemethylhydrazone (as prepared in Example 47A, above), 60.5 g of allyl bromide and 50.5 g of triethylamine were dissolved in 1 liter of acetonitrile and the mixture was heated at reflux temperature for 16 hours, then cooled. An additional 45 g of allyl bromide and 38 g of triethylamine were added and the mixture was again heated at reflux for an additional 7 hours, allowed to cool and then stripped of solvent to yield 268 g of a residue. To this residue was added 500 ml of THF and the resultant mixture was shaken, filtered and washed with an additional 125 ml of THF. The filtrate was stripped of solvent to yield 67 g of the desired subtitled intermediate.

C. Preparation of N-methyl, N-2-propenylhydrazine 59.9 g of benzaldehyde N-methyl, N-2-propenylhydrazone (prepared as described in Example 47B, above), 44 g of hydrazine and 137 ml of ethanol were heated at reflux temperature for 21.5 hours and allowed to cool. The reflux condenser was replaced with a distillation head and the mixture was distilled at atmospheric pressure. The first three distillates were collected, combined and 100 ml of 1N HCl were added. An additional 100 ml of concentrated HCl was added, with ice, and the resultant mixture separated and washed with a small amount of ethyl acetate. The resultant layers were separated and the water distilled off until solids clogged the stir bar. The solids were filtered off and the filtrate was stripped and added to 125 ml of chilled 50% NaOH. The resulting solid was filtered off and discarded. The filtrate contained two layers which were separated. The top layer contained the desired subtitled intermediate and the bottom, aqueous layer was extracted with diethyl ether which, upon stripping, gave additional product.

D. Preparation of N-Methyl, N-3-propenyl-5-carboxymethyl-dithiocarbamate

To 12.67 g of N-methyl, N-2-propenylhydrazine (prepared as described in Example 47C) in 23 ml of ethanol chilled to 0° C. was added a solution of 11.18 g of carbon disulfide in 26 ml of diethyl ether. The resultant mixture was removed from the ice bath and allowed to stand at room temperature for about 15.5 hours, after which the solvent was stripped to yield a residue of approximately 36.5 g. To this residue was added 13.9 g of chloroacetic acid dissolved in 29.5 ml of 5N NaOH (chilled in an ice bath). The resultant solution was allowed to stand for 3 hours at room temperature. The pH of the solution was reduced to about 3 by the addition of 8 ml of concentrated hydrochloric acid. To this was added 50 ml of diethyl ether, resulting in a three phase separation. The aqueous phases were pooled and extracted with an additional 50 ml of chloroform, then stripped of solvent to yield approximately 40.4 g of the desired subtitled intermediate.

E. Preparation of 5-[[3,5-bis(1,1-dimethylethyl)-4-hydroxyphenyl]methylene]-2-thioxo-3-(methyl-2-propenylamino)-4-thiazolidinone 29.3 g of 3,5-di-tert-butyl-4-hydroxybenzaldehyde, 38.8 g of the intermediate prepared as described in Example 47D, above, and 40.34 g of sodium acetate were mixed in 810 ml of acetic acid and the resultant solution was heated at reflux temperature for 24 hours. The solution was then allowed to cool and stirred for an additional 60 hours at room temperature. The solution was then poured into 2 l of ice water, separated and washed with an additional volume of water to yield about 44 g of the desired subtitled intermediate.

F. Preparation of 5-[[3,5-bis(1,1-dimethylethyl)-4-hydroxyphenyl]methylene]-3-(methyl-2-propenylamino)-4-thiazolidinone Utilizing the procedure described in Example 40E, and elsewhere herein, 42.8 g of the thione of Example 47E, above, was reduced to the desired subtitled intermediate (8.34 g).

G. Preparation of 5-[[3,5-bis(1,1-dimethylethyl)-4-hydroxyphenyl]methylene]-3-(methylamino)-4-thiazolidinone 6.11 g of the subtitled intermediate of Example 47F was dissolved in a mixture of 135 ml ethanol and 15.3 ml of water and the mixture heated to 70° C. 50 mg of tris(triphenylphosphine)rhodium (I) chloride was added and the mixture heated at reflux temperature for 50 minutes, after which an additional 550 mg of the catalyst was added followed by heating at reflux temperature for an additional 2.5 hours. The mixture was cooled, stirred at room temperature overnight and stripped of solvent to give 2.05 g of the desired product after further workup, m.p. 151°–153.5° C.

Analysis for $C_{19}H_{28}N_2O_2S$: Calculated: C, 65.86; H, 7.56; N, 8.09; Found: C, 65.67; H, 7.81; N, 8.34.

Utilizing the procedures set forth herein, the following additional compounds were prepared.

EXAMPLE 48

5-[[3,5-bis(1,1-dimethylethyl)-4-hydroxyphenyl]methylmethylene]-4-thiazolidinone, m.p. >230° C.

Analysis for $C_{19}H_{27}NO_2S$: Calculated: C, 68.43; H, 8.16; N, 4.20; Found: C, 68.60; H, 8.28; N, 4.17.

EXAMPLE 49

5-[[3,5-bis(1,1-dimethylethyl)-4-hydroxyphenyl]methylene]-3-[(2-(4-morpholinyl)ethyl]-4-thiazolidinone, m.p. 218°–222° C. (dec.)

Analysis for $C_{24}H_{36}N_2O_3S$: Calculated: C, 66.83; H, 8.39; N, 6.48; Found: C, 66.58; H, 8.15; N, 6.67.

EXAMPLE 50

3-amino-5-[[3,5-bis(1,1-dimethylethyl)-4-hydroxyphenyl]methylene]-4-thiazolidinone, m.p. 162°–164° C.

Analysis for $C_{18}H_{26}N_2O_2S$: Calculated: C, 64.64; H, 7.84; N, 8.38; Found: C, 64.85; H, 7.92; N, 8.19.

EXAMPLE 51

5-[[3,5-bis(1,1-dimethylethyl)-4-hydroxyphenyl]methylene]-3-(propylamino)-4-thiazolidinone, m.p. 131°–136° C.

Analysis for $C_{21}H_{32}N_2O_2S$: Calculated: C, 66.98; H, 8.57; N, 7.44; Found: C, 67.22; H, 8.70; N, 7.37.

EXAMPLE 52

5-[[3,5-bis(1,1-dimethylethyl)-4-hydroxyphenyl]methylene]-3-(ethylamino)-4-thiazolidinone, m.p. 125°–127° C.

Analysis for $C_{20}H_{30}N_2O_2S$: Calculated: C, 66.26; H, 8.34; N, 7.73; Found: C, 66.46; H, 8.35; N, 7.95.

EXAMPLE 53

5-[[3,5-bis(1,1-dimethylethyl)-4-hydroxyphenyl]methylene]-3-(dimethylamino)-2-thioxo-4-thiazolidinone, m.p. 158°–160° C.

Analysis for $C_{20}H_{28}N_2O_2S$: Calculated: C, 61.19; H, 7.19; N, 7.14; Found: C, 61.33; H, 7.23; N, 7.43.

EXAMPLE 54

5-[3,5-bis(1,1-dimethylethyl)-4-hydroxyphenyl]methylene]-3-[(2-hydroxyethyl)amino]-4-thiazolidinone, m.p. 128°–132° C.

Analysis for $C_{20}H_{30}N_2O_3S$: Calculated: C, 63.46; H, 7.99; N, 7.40; Found: C, 63.57; H, 7.92; N, 7.45.

EXAMPLES 55–56

5-[(3,5-di-2-propenyl-4-hydroxyphenyl)methylene]-4-thiazolidinone and 5-[(3,5-di-2-propenyl-4-hydroxyphenyl)methyl]-4-thiazolidinone A. Preparation of 3,5-di-(2-propenyl)-4-hydroxybenzaldehyde Under a nitrogen atmosphere and using a mechanical stirrer, 250 g of parahydroxybenzaldehyde, 247.6 g of allyl bromide, 311.7 g of potassium bicarbonate and 650 ml of acetone were heated to reflux temperature for about 18 hours. The mixture was allowed to cool, after which about 1 liter of water was added followed by extraction with two 800 ml portions of diethyl ether. Subsequent distillation of the organic phase rendered about 299 g of 4-(2-propenyl)oxybenzaldehyde which was then heated with about 300 ml of diethylaniline for 5.5 hours at 195°–205° C. The mixture was cooled and 750 ml of ethyl acetate was added. The mixture was washed with three 500 ml portions of 1N HCl which, followed by subsequent workup, yielded about 138 g of 3-(2-propenyl)-4-hydroxybenzaldehyde. The monosubstituted aldehyde (159 g) was again heated to reflux with 152 g of potassium carbonate and 465 ml of acetone for 3 hours and then allowed to cool. The mixture was poured into 900 ml of ice water and subsequently extracted with two 430 ml portions of diethyl ether to yield about 170 g of 3-(2-propenyl)-4-(2-propenyloxy)benzaldehyde. The disubstituted aldehyde was then heated in about 500 ml of diethylaniline, under a nitrogen atmosphere, to 195°–205° C. for about 6.5 hours. The mixture was cooled and dissolved in about 800 ml of ethyl acetate, washed with three 1 liter portions of 1N HCl and, following workup, rendered about 121.9 g of the desired subtitled intermediate.

B. Preparation of 5-[(3,5-di-2-propenyl-4-hydroxyphenyl)methylene]-4-thiazolidinone and 5-[(3,5-di-2-propenyl-4-hydroxyphenyl)methyl]-4-thiazolidinone 3,5-di-(2-propenyl)-4-hydroxybenzaldehyde (50.5 g), 36.6 g of rhodanine and 164 g of sodium acetate were heated together at reflux temperature in 1.25 liter of acetic acid for 14.5 hours. The resultant solution was cooled, poured into 2 liter of ice water to yield, upon separation, about 75 g of 5-[(3,5-di-2-propenyl-4-hydroxyphenyl)-methylene]-2-thioxo-4-thiazolidinone, m.p. 157°–160° C.

The thione produced above (74.8 g) was reduced by treatment with zinc dust (62 g) and concentrated hydrochloric acid (950 ml) in 2.1 liters of hot (approximately 82° C.) ethanol. Once the reactants were combined the solution was allowed to cool to room temperature, stirred for one hour, and then added to 3.75 liters of ice water. The resulting solution was allowed to sit overnight to provide a gum. The liquid layer was decanted and extracted with 750 ml of chloroform, while the gum was dissolved in 560 ml of chloroform and the resulting solution was washed, successively, with 75 ml of a saturated sodium carbonate solution, 75 ml of water and 75 ml of a saturated brine solution. The above chloroform solutions were combined and then triturated with 100 ml of methylene chloride. The titled products were obtained using silica gel chromatography. Elution with a 25–60% ethyl acetate in hexane gradient provided various fractions which were treated as follows.

Fractions 13–15 were concentrated and then washed with ethyl acetate to provide 2.91 g of 5-[(3,5-di-2-propenyl-4-hydroxyphenyl)methyl]-4-thiazolidinone. Fractions 16–18 were concentrated to a residue which was triturated with 30 ml of methylene chloride. Fractions 19–23 were concentrated to a residue which was triturated with 35 ml of methylene chloride. Following trituration, the remaining insolubles were isolated by filtration and triturated with 40 ml of ethyl acetate to provide 3.85 g of 5-[(3,5-di-2-propenyl-4-hydroxyphenyl)methylene]-4-thiazolidinone.

The ethyl acetate wash from fractions 13–15, the methylene chloride solution containing fractions 16–18 and the methylene chloride and ethyl acetate solutions obtained from fractions 19–23 were combined and loaded onto a silica gel chromatography column. Elution with a 1:1 ethyl acetate/hexane solution provided various fractions which were combined according to the purities of the respective compounds. Fractions which were predominately 5-[(3,5-di-2-propenyl-4-hydroxyphenyl)methyl]-4-thiazolidinone were crystallized from hot ethyl acetate to provide 1.24 g of that compound (total yield of 5-[(3,5-di-2-propenyl-4-hydroxyphenyl)methyl]-4-thiazolidinone - 4.14 g). Fractions which were predominately 5-[(3,5-di-2-propenyl-4-hydroxyphenyl)methylene]-4-thiazolidinone were triturated with 30 ml of hot ethyl acetate to provide 1.73 g of that compound (total yield of 5-[(3,5-di-2-propenyl-4-hydroxyphenyl)methylene]-4-thiazolidinone-5.58 g).

55. 5-[(3,5-di-2-propenyl-4-hydroxyphenyl)methylene]-4-thiazolidinone, m.p. 184°–188° C.

Analysis for $C_{16}H_{17}NO_2S$: Calculated: C, 66.87; H, 5.96; N, 4.87; Pound: C, 66.62, H, 5.92; N, 4.89.

56. 5-[(3,5-di-2-propenyl-4-hydroxyphenyl)methyl]-4-thiazolidinone, m.p. 142°–144° C.

Analysis for $C_{16}H_{19}NO_2S$: Calculated: C, 66.41; H, 6.62; N, 4.84; Found: C, 66.18; H, 6.69; N, 4.60.

Utilizing the procedures set forth in Examples 55 and 56 and elsewhere herein, the following additional compounds were prepared.

EXAMPLE 57

5-[(3,5-di-2-propenyl-4-hydroxyphenyl)methylene]-3-methyl-4-thiazolidinone, m.p. 155°–159° C.

Analysis for $C_{17}H_{19}N_2S$: Calculated: C, 67.74; H, 6.35; N, 4.65; Found: C, 67.53; H, 6.09; N, 4.45.

EXAMPLE 58

5-[(3,5-dipropyl-4-hydroxyphenyl)methylene]-3-methyl-4-thiazolidinone, m.p. 162°–165° C.

Analysis for $C_{17}H_{23}NO_2S$: Calculated: C, 66.85; H, 7.59; N, 4.59; Found: C, 67.12; H, 7.37; N, 4.52.

EXAMPLE 59

5-[(3,5-dipropyl-4-hydroxyphenyl)methylene]-4-thiazolidinone, m.p. 202°–205° C.

Analysis for $C_{16}H_{23}NO_2S$: Calculated: C, 65.95; H, 7.26; N, 4.81; Found: C, 66.16; H, 7.49; N, 4.79.

EXAMPLE 60

5-[(3,5-dipropyl-4-hydroxyphenyl)methyl]-4-thiazolidinone, m.p. 155°–157° C.

Analysis for $C_{16}H_{23}NO_2S$: Calculated: C, 65.49; H, 7.90; N, 4.77; Found: C, 65.71; H, 7.73; N, 4.99.

EXAMPLE 61

5-[[3-(1,1-dimethylethyl)-4-hydroxy-5-methylphenyl]methylene]-4-thiazolidinone.

A. Preparation of 3-(1,1-dimethylethyl)-4-hydroxy-5-methylbenzaldehyde

Under a nitrogen atmosphere, 76.65 g of 2-(1,1-dimethylethyl)-6-methylphenol (Aldrich), 65.42 g of hexamethylenetetramine and 700 ml of trifluoroacetic acid were stirred at reflux temperature for about 24 hours, then allowed to cool and evaporated. The residue from the evaporation was taken up in 1500 ml of water and 1000 ml of chloroform and neutralized to pH 7 with solid sodium carbonate. The resultant layers were separated and the aqueous layer was washed with chloroform. The organic layer was dried over sodium sulfate overnight, after which it was again washed with a volume of chloroform and evaporated. The resultant residue was then taken up in 375 ml of toluene, heated on a steam bath and then allowed to cool to room temperature overnight. Subsequent workup gave 28.3 g of the desired subtitled intermediate.

B. Preparation of 5-[[3-(1,1-dimethylethyl)-4-hydroxy-5-methylphenyl]methylene]-2-thioxo-4-thiazolidinone 28.3 g of the intermediate prepared in Example 61A, 24 g of N-aminorhodanine, 48.3 g of sodium acetate in 735 ml of acetic acid were heated to reflux temperature for about 7 hours and then allowed to cool to room temperature with continual stirring overnight. The resultant mixture was poured into 1500 ml of ice water with stirring and then filtered. The wet filter cake was transferred to a beaker and dissolved in a mixture of ethyl acetate and water and then separated. The organic layer was dried over sodium sulfate, filtered and then washed with ethyl acetate. Further workup, followed by trituration in hot chloroform and subsequent drying under vacuum; rendered about 18 g of the desired subtitled intermediate, m.p. 210°–216° C.

C. Preparation of 5-[[3-(1,1-dimethylethyl)-4-hydroxy-5-methylphenyl]methylene]-4-thiazolidinone.

Reduction of the thione of Example 61B as described herein was effected which, following workup, rendered 1.56 g of the titled product, m.p. 162°–165° C.

Analysis for $C_{25}H_{19}NO_2S$: Calculated: C, 64.95; H, 6.90; N, 5.05; Found: C, 65.12; H, 7.05; N, 4.99.

Utilizing the procedures set forth in Example 61 and elsewhere herein, the following additional compounds were prepared.

EXAMPLE 62

3-amino-5-[[3-(1,1-dimethylethyl)-4-hydroxy-5-methylphenyl]methylene]-4-thiazolidinone, m.p. 110° C. (dec.)

Analysis for $C_{15}H_{20}N_2O_2S$: Calculated: C, 61.81; H, 7.29; N, 9.01; Found: C, 61.90; H, 7.47; N, 8.78.

EXAMPLE 63

5-[[3-(1,1-dimethylethyl)-4-hydroxy-5-methylphenyl]methylene]-3-dimethylamino-2-thioxo-4-thiazolidinone, m.p. 189°–190° C.

Analysis for $C_{17}H_{22}N_2O_2S$: Calculated: C, 58.26; H, 6.33; N, 7.99; Found: C, 58.55; H, 6.08; N, 8.28.

EXAMPLE 64

5-[[3-(1,1-dimethylethy)-4-hydroxy-5-methylphenyl]methylene]-3-methyl-4-thiazolidinone, m.p. 192°–195° C.

Analysis for $C_{16}H_{21}NO_2S$: Calculated: C, 65.95; H, 7.26; N, 4.81; Found: C, 66.24; H, 7.17; N, 5.02.

EXAMPLE 65

5-[[3-(1,1-dimethylethyl)-4-hydroxy-5-methylphenyl]methylene]-3-dimethylamino-4-thiazolidinone, m.p. 182°–192° C.

Analysis for $C_{17}H_{24}N_2O_2S$: Calculated: C, 63.72; H, 7.55; N, 8.74; Found: C, 63.45; H, 7.58; N, 8.93.

EXAMPLE 66

5-[[3,5-bis(1-methylethyl)-4-hydroxypheny]methyl]-2-thioxo-4-thiazolidinone

EXAMPLE 67

5-[[3-(methylthiophenyl)-4-hydroxy-5-ethoxyphenyl]methylene]-2-thioxo-3-(dimethylamino)-4-thiazolidinone, m.p. 137°–141° C.

Analysis for $C_{21}H_{22}N_2O_3S_3$: Calculated: C, 56.48; H, 4.97; N, 6.27; Found: C, 56.77; H, 5.07; N, 5.99.

EXAMPLE 68

5-[[3-(methylthiophenyl-4-hydroxy-5-ethoxyphenyl]methylene]-4-thiazolidinone, m.p. 190°–192° C.

Analysis for $C_{19}H_{17}N_3S_3$: Calculated: C, 56.55; H, 4.25; N, 3.47; Found: C, 56.76; H, 4.42; N, 3.44.

EXAMPLE 69

5-[[3-(1,1-dimethylethyl)-4-hydroxy-5-propylphenyl]methylene]-3-methyl-4-thiazolidinone, m.p. 189.5°–191.5° C.

Analysis for $C_{18}H_{25}NO_2S$: Calculated: C, 67.68; H, 7.89; N, 4.38; Found: C, 67.97; H, 8.16; N, 4.40.

EXAMPLE 70

5-[[3-(1,1-dimethylethyl)-4-hydroxyphenyl]methylene]-3-methyl-4-thiazolidinone.

A. Preparation of 3-(1,1-dimethylethyl)-4-hydroxybenzaldehyde

Into 101.5 g of N-methylformanilide was added dropwise with cooling 107 g of phosphoryl chloride over a period of 15 minutes. The mixture was allowed to warm to room temperature and stirred for 70 minutes. 67.5 g of ortho-t-butylphenol was added and stirred for about 45 minutes after which the mixture was heated to about 50°–60° C. and allowed to stir for 4.5 hours. The reaction mixture was poured into a volume of crushed ice and extracted with chloroform. The aqueous layer was separated and washed again with chloroform. The chloroform layers were combined and extracted with 2000 ml of a 5% potassium hydroxide solution. The aqueous potassium hydroxide layer was separated and added to 1000 ml of chloroform. The pH of the resulting two-phase mixture was adjusted to 3 with concentrated hydrochloric acid with stirring. The resultant layers were separated and the aqueous layer was again extracted with chloroform and dried over sodium sulfate overnight to give 18.1 g of the desired subtitled intermediate.

B. Preparation of 5-[[3-(1,1-dimethylethyl)-4-hydroxyphenyl]methylene]-3-methyl-2-thioxo-4-thiazolidinone.

The benzaldehyde intermediate from Example 70A (17.5 g) was dissolved in 490 ml of acetic acid. The resulting solution was added to a mixture of 14.45 g of N-methylrhodanine and 28.18 g of sodium acetate. The resultant suspension was heated, stirred at reflux temperature for 24 hours (at which time a yellow precipitate had formed), filtered and washed with acetic acid and diethyl ether. The precipitate was triturated with 300 ml of diethyl ether, filtered, washed again with diethyl ether and triturated yet a second time with 600 ml of water. Drying the resultant solid in vacuo yielded the desired subtitled intermediate, m.p. >230° C.

C. Preparation of 5-[[3-(1,1-dimethylethyl)-4-hydroxyphenyl]methylene]-3-methyl-4-thiazolidinone.

The thione prepared in Example 70B was reduced as described above utilizing tri-n-butyl tin hydride and AIBN to provide the desired title product, m.p. >230° C.

Analysis for $C_{15}H_{19}NO_2S$: Calculated: C, 64.95; H, 6.90; N, 5.05; Found: C, 65.07; H, 7.02; N, 5.28.

Utilizing the procedures set forth herein, the following additional compounds were prepared.

EXAMPLE 71

5-[[3-(methylthiophenyl)-4-hydroxy-5-ethoxyphenyl]methylene]-4-oxo-2-thioxo-3-thiazolidine acetic acid, m.p. 202°–206° C.

Analysis for $C_{21}H_{19}NO_5S_3$: Calculated: C, 54.65; H, 4.15; N, 3.04; Found: C, 54.91; H, 4.23; N, 3.11.

EXAMPLE 72

5-[(4-hydroxy-3,5-dimethylphenyl)methylene]-3-methyl-4-thiazolidinone, m.p. 207°–212° C. (dec.)

Analysis for $C_{13}H_{15}NO_2S$: Calculated: C, 62.62; H, 6.06; N, 5.62; Found: C, 62.58; H, 6.05; N, 5.65.

EXAMPLE 73

5-[[3-(1,1-dimethylethyl)-4-hydroxy-5-methylphenyl]methyl]-4-thiazolidinone

A solution of 0.28 g of the compound of Example 61 in 30 ml of tetrahydrofuran was hydrogenated at 60 pounds per square inch in the presence of 1.12 g of 5% palladium on carbon overnight at 60° C. The reaction mixture was filtered and evaporated to dryness. The resulting residue was dissolved in 3.5 ml of a 1:1.5 ethyl acetate/hexane solution and loaded onto a silica gel chromatography column. Elution with 40% ethyl acetate in hexane produced fractions which, upon evaporation to dryness, provided 0.05 g of title compound. m.p. 64°–68° C.

Analysis for $C_{15}H_{21}NO_2S$: Calculated: C, 64.48; H, 7.58; N, 5.01; Found: C, 64.32; H, 7.66; N, 4.79.

EXAMPLE 74

5-[[3,5-bis(1-methylethyl)-4-hydroxyphenyl]methyl]-4-thiazolidinone

Using the method described in Example 73, 4.73 g of 5-[[3,5-bis(1-methylethyl)-4-hydroxyphenyl]methylene]-4-thiazolidinone were converted to 1.88 g of title compound. m.p. 136°–139° C.

Analysis for $C_{16}H_{23}NO_2S$: Calculated: C, 65.49; H, 7.90; N, 4.77; Found: C, 65.79; H, 7.90; N, 4.81.

EXAMPLE 75

5-[[3-(1,1-dimethylethyl)-4-hydroxy-5-propylphenyl] methyl]-4-thiazolidinone

A. Preparation of 3-[2-(1,1-dimethylethyl) phenoxypropene

Allyl bromide (69.2 ml), 2-t-butylphenol (122.9 ml) and potassium carbonate (121.6 g) were stirred in 265 ml of acetone at reflux temperature for 50 hours and then cooled to 35° C. Water (600 ml) was added and the resulting layers were separated. The aqueous layer was extracted with 600 ml of diethyl ether. The organic layer was combined with the aqueous layer's ether extract and the resulting solution was dried over sodium sulfate overnight. After sodium sulfate removal, the solvent was evaporated to provide, after further workup, 147 g of the subtitled intermediate.

B. Preparation of 2-(1,1-dimethylethyl)-6-(2-propenyl) phenol

All 147 g of the above compound were rearranged as described in Examples 55A and 56A to provide 100.8 g of the subtitled intermediate.

C. Preparation of 2-(1,1-dimethylethyl)-6-propylphenol.

A solution of 54.9 g of the above compound in 575 ml of toluene was hydrogenated at 60 pounds per square inch in the presence of 55 g of Raney nickel for 3 hours at room temperature. The reaction mixture was filtered and evaporated to dryness to provide 59.2 g of the subtitled intermediate.

D. Preparation of 3-(1,1-dimethylethyl)-4-hydroxy-5-propylbenzaldehyde.

The above compound (55.48 g) was converted to 23.33 g of the subtitled intermediate using the method described in Example 61A.

E. Preparation of 5-[[3-(1,1-dimethylethyl)-4-hydroxy-5-propylphenyl]methylene]-2-thioxo-4-thiazolidinone.

Using the method described in Example 61B, 5.51 g of the above compound were converted to 6.26 g of the subtitled intermediate. m.p. 190.5°–192° C.

F. Preparation of 5-[[3-(1,1-dimethylethyl-4-hydroxy-5-propylphenyl]methyl]-2-thioxo-4-thiazolidinone.

Using the method described in Example 8, 4.73 g of the above compound were converted to 2.1 g of the subtitled intermediate.

G. Preparation of 5-[[3-(1,1-dimethylethyl-4-hydroxy-5-propylphenyl]methyl]-4-thiazolidinone.

A solution of 2.1 g of the above compound in 185 ml of ethanol was hydrogenated at 500 pounds per square inch in the presence of 8.4 g of 5% palladium on carbon for 20 hours at 100° C. The reaction mixture was filtered and evaporated to dryness. The resulting residue was dissolved in 25 ml of methylene chloride and loaded onto a silica gel chromatography column. Elution with 2000 ml of a 10–50% ethyl acetate in hexane gradient, followed by elution with 2000 ml of a 1:1 ethyl acetate/hexane solution, provided fractions which, upon evaporation to dryness, rendered 0.75 g of titled product. m.p. 50°–55° C.

Analysis for $C_{17}H_{25}NO_2S$: Calculated: C, 66.41; H, 8.20: N, 4.56; Found: C, 66.61; H, 8.22; N, 4.55.

EXAMPLE 76

5-[[3-(methylthiophenyl)-4-hydroxy-5-ethoxyphenyl] methylene]-3-dimethylamino-4-thiazolidinone.

A. Preparation of 5-[[3-ethoxy-4-hydroxyphenyl] methylene]-3-dimethylamino-2-thioxo-4-thiazolidinone.

3-Ethoxy-4-hydroxybenzaldehyde (45.7 g), N-dimethylaminorhodanine (53.35 g) and fused sodium acetate (92.4 g) were reacted in the manner described in Example 1 to provide 52.92 g of the subtitled intermediate. m.p. 194°–198° C.

B. Preparation of 5-[[3-ethoxy-4-hydroxyphenyl] methylene]-3-dimethylamino-4-thiazolidinone.

Using the method described in Example 10, 47.66 g of the above compound were converted to 14.02 g of the subtitled intermediate.

C. Preparation of 5-[[3-methylthiophenyl)-4-hydroxy-3-ethoxyphenyl]methylene]-3-dimethylamino-4-thiazolidinone.

Sodium hydroxide (0.95 g) and 17.3 ml of a 40% by weight solution of formaldehyde were dissolved in 50 ml of 2-ethoxyethanol. Phenylthiol (2.62 g) and 7.0 g of the above compound were added and the resulting solution was refluxed for 4 hours, then cooled. Ethyl acetate (50 ml) and water (25 ml) were added to the cooled reaction mixture and the pH of the resulting two-phase solution was lowered to approximmately 5 using concentrated hydrochloric acid. The organic phase was separated from the aqueous phase, washed with a saturated brine solution and then loaded onto a silica gel chromatography column. Elution with 4 liters of methylene chloride, followed by 4 liters of a 3% methanol/ 97% methylene chloride solution, provided fractions containing the title product. These fractions were combined and loaded once more onto a silica gel chromatography column. Elution with 4 liters of methylene chloride, followed by 1 liter of a 22.5% acetonitrile in methylene chloride solution, provided fractions which, upon evaporation of the solvent, rendered title product. This product was further purified by trituration with a hot solution of 50 ml of hexane and 30 ml of ethyl acetate to provide 6.20 g of 5-[[3-(methylthiophenyl)-4-hydroxy-5-ethoxyphenyl]methylene]-3-dimethylamino-4-thiazolidinone. m.p. 118°–120° C.

Analysis for $C_{21}H_{24}N_2O_3S_2$: Calculated: C, 60.55; H, 5.81; N, 6.73; S, 15.39; Found: C, 60.75; H, 5.76; N, 6.76; S, 15.58.

EXAMPLE 77

5-[[3-(1-dimethylethyl)-4-hydroxyphenyl]methylene]-4-thiazolidinone

A. Preparation of 3-(1,1-dimethylethyl)-4-hydroxybenzaldehyde

Into 184.4 ml (1,494 mol) of N-methylformanilide were added dropwise, with cooling, 130.9 ml (1,404 mol) of phosphoryl chloride over a period of 20 minutes. The mixture was allowed to warm to room temperature and stirred for one hour. Ortho-tertbutylphenol (138.2 ml; 0.9 mol) was then added dropwise to the reaction solution over a period of 25 minutes. After phenol addition was complete, the resulting reaction mixture was stirred for an additional 30 minutes at room temperature and then heated to approximately 60° C. and stirred for five hours at that temperature. The reaction mixture was poured into a volume of crushed ice and extracted with chloroform. The aqueous layer was separated and washed again with chloroform. The chloroform layers were combined and extracted with 2000 ml of a 5% potassium hydroxide solution. The aqueous potassium hydroxide extract was then added to 1000 ml of chloroform. The pH of the resulting two-phase mixture was adjusted to approximately pH 2.0 with concentrated hydrochloric acid. The mixture's layers were separated and the aqueous layer was again extracted with chloroform. The organic layer from the two-phase mixture and the chloroform extract were combined, washed with water and then dried over sodium sulfate. The volatile components of the solution were removed under reduced pressure to provide a residue. This residue was dissolved in 100 ml of hot toluene and the resulting solution was diluted with 100 ml of hexanes. The solution was slowly cooled to room temperature while a precipitate formed. This precipitate was recovered by filtration, washed with hexanes and then dried under vacuum to provide 20.0 g of the desired substituted intermediate.

B. Preparation of 5-[[3-(1,1-dimethylethyl)-4-hydroxyphenyl]methylene]-3-amino-2-thioxo-4-thiazolidinone The benzaldehyde intermediate from Example 77A (20.0 g; 112.2 mmol), N-aminorhodanine (18.29 g; 123.4 mmol) and sodium acetate (36.8 g; 448.8 mmol) were suspended in 560 ml of acetic acid. The suspension was heated to reflux, stirred at that temperature for 7 hours (at which time a precipitate had formed) and then cooled to room temperature with stirring. The precipitate was recovered by filtration and then washed successively with a 1:1 ethyl acetate/diethyl ether solution then a diethyl ether wash. The recovered precipitate was dried under vacuum at 60° C. for 2 hours to provide 14.5 g of the desired subtitled intermediate. m.p. >225° C.

C. Preparation of 5-[[3-(1,1-dimethylethyl)-4-hydroxyphenyl]methylene]-4-thiazolidinone The intermediate from Example 77B (14.3 g; 46.4 mmol) was suspended in 230 ml of hot (60° C.) toluene. To this suspension were added tri-n-butyl tin hydride (62.4 ml; 232 mmol) and AIBN (1.14 g; 6.96 mmol). The resulting suspension was heated to reflux while the suspended solids slowly dissolved. Additional AIBN was added at 30 and 55 minutes (two 1.14 g portions) after heating was started. Eighty minutes after heating was started the hot reaction solution was transferred to a separatory funnel and 1N hydrochloric acid was added. The resulting two-phase mixture was diluted with ethyl acetate and the layers were separated. The aqueous layer was washed with ethyl acetate, which wash was then combined with the organic layer from the two-phase mixture. The combined solution was washed with a saturated sodium chloride solution and then dried over sodium sulfate. The volatile components of the solution were removed under reduced pressure to provide 87.7 g of a yellow solid. This solid was suspended in 1000 ml of hexanes and the resulting suspension was stirred for 15 minutes. After fifteen minutes the suspension was filtered and the recovered solid was dissolved in 500 ml of diethyl ether. The diethyl ether solution was chromatographed on a silica gel column using an 8000 ml gradient of 5–20% isopropyl alcohol in hexanes, then a 2000 ml gradient of 20–30% isopropyl alcohol in hexanes and then a 2000 ml gradient of 30–35% isopropyl alcohol in hexanes. Those fractions identified as containing product were evaporated and chased with methylene chloride. The resulting residue was dissolved in ethyl acetate, reduced to dryness under reduced pressure and then chased with ethanol to provide 4.31 g of title compound. m.p. 110° C. (decomposition).

Analysis for $C_{14}H_{17}NO_2S$: Calculated: C, 63.85; H, 6.51; N, 5.32; Found: C, 64.15; H, 6.73; N, 5.60.

EXAMPLE 78

5-[[3-(1,1-dimethylethyl)-4-hydroxyphenyl]methyl]-4-thiazolidinone

A portion of the title compound from Example 77 (395.1 mg; 1.5 mmol) was dissolved in 9 ml of methanol. Magnesium (72.9 mg; 3.0 mmol) was then added to the solution and the resulting reaction mixture was stirred at room temperature for 3 hours. After 3 hours, most of the magnesium which had been added originally appeared to be gone so an additional 182.3 mg (7.5 mmol) of magnesium were added. Stirring of the reaction solution at room temperature continued overnight. By the next morning a yellow precipitate had formed. This precipitate was dissolved by adding the methanolic reaction solution to an ethyl acetate/1N hydrochloric acid mixture. The organic layer from the resulting two-phase mixture was isolated and then dried over sodium sulfate. The volatile components of the organic layer were removed and the resulting residue was chased with methylene chloride. The residue was then dissolved in 25 ml of methylene chloride and the resulting solution was chromatographed on a silica gel chromatography column using a 5–20% isopropyl alcohol in hexanes gradient. Those fractions identified as containing essentially pure product were evaporated to provide 0.29 g of title compound. m.p. 65°–70° C.

Analysis for $C_{14}H_{19}NO_2S$: Calculated: C, 63.37; H, 7.22; N, 5.28; Found: C, 63.08; H, 7.30; N, 4.99.

EXAMPLE 79

(−)-5-[[3,5-bis(1,1-dimethylethyl)-4-hydroxyphenyl]methyl]-4-thiazolidinone.

To a 50 ml, three-neck, round bottom flask containing 25 ml of methylene chloride were added 1.31 g of 4 Å molecular sieves, 0.56 ml (1.88 mmol) of titanium isopropoxide, 0.79 ml (3.75 mmol) of (+)-diisopropyl tartrate and 34 1 (1.88 mmol) of deionized water. The resulting solution was stirred for twenty minutes and then 0.8 g (2.5 mmol) of a racemic mixture of 5-[[3,5-bis(1,1-dimethylethyl)4-hydroxyphenyl]methyl-4-thiazolidinone were added. The resulting solution was cooled to −20° C. and 0.73 ml (1.88 mmol) of a 2.57M solution of t-butylhydroperoxide in isooctane were added. The reaction solution was then stirred for 6 hours at −20° C.

After 6 hours, the reaction solution was quenched by pouring it into 50 ml of a solution prepared from 9.9 g of Iron (II) sulfate heptahydrate, 3.3 g of citric acid monohydrate and water. The resulting solution was stirred for 30 minutes and then stirring was stopped so that the organic and aqueous layers could separate. The aqueous layer was decanted and washed with methylene chloride. The methylene chloride wash was combined with the above organic layer and the resulting solution was washed with a saturated brine solution and then dried over sodium sulfate. The sodium sulfate was removed by filtration and the remaining liquid was evaporated to provide 1.81 g of a residue.

The residue was dissolved in 25 ml of methylene chloride and the resulting solution was chromatographed on a silica gel chromatography column. Elution with 6000 ml of a 10–50% ethyl acetate in hexane gradient provided various fractions containing the above titled compound. These fractions were combined and the liquid evaporated to provide 0.19 g of title compound. $[\alpha]^{25}=−73.6°$ (c=1.0, MeOH).

Analysis for $C_{18}H_{27}NO_2S$: Calculated: C, 67.25; H, 8.47; N, 4.36; Found: C, 67.50; H, 8.53; N, 4.48.

EXAMPLE 80, 81, and 82

(+)-5-[[3,5-bis(1,1-dimethylethyl)-4-hydroxyphenyl]methyl]-4-thiazolidinone, (−)-5-[[3,5-bis(1,1-dimethylethyl)-4-hydroxyphenyl]methyl]-4-thiazolidinone-1-oxide and (+)-5-[[3,5-bis(1,1-dimethylethyl)-4-hydroxyphenyl]methyl]-4-thiazolidinone-1-oxide.

In a similar manner as that described in Example 79, 0.89 ml (3.0 mmol) of titanium isopropoxide, 1.27 ml (6.0 mmol) of (−)-diisopropyl tartrate, 54 1 (3.0 mmol of deionized water, 1.61 g (5.0 mmol) of racemic 5-[[3,5-bis(1,1-dimethylethyl)-4-hydroxyphenyl]methyl-4-thiazolidinone and 2.4 ml (6.5 mmol) of a 2.57M solution of t-butylhydroperoxide in isooctane were reacted to provide a residue. The residue was dissolved in 75 ml of methylene chloride and the resulting solution was chromatographed on a silica gel chromatography column. Elution with 6000 ml of a 10–50% ethyl acetate in hexane gradient provided various fractions containing (+)-5-[[3,5-bis-(1,1-dimethylethyl)-4-hydroxyphenyl]methyl-4-thiazolidinone. These fractions were combined and the liquid evaporated to provide 0.43 g of product compound. Further elution with 4000 ml of a 50% isopropanol in hexane solution provided various fractions. Fractions believed to contain (−)-5-[[3,5-bis(1,1-dimethylethyl)-4-hydroxyphenyl]methyl]-4-thiazolidinone-1-oxide were combined and the liquid evaporated to provide 0.87 g of product. Fractions believed to contain (+)-5-[[3,5-bis(1,1-dimethylethyl)-4-hydroxyphenyl]methyl]-4-thiazolidinone-1-oxide were combined and the liquid evaporated to provide 0.27 g of product.

80. (+)-5-[[3,5-bis(1,1-dimethylethyl)-4-hydroxyphenyl]methyl]-4-thiazolidinone $[\alpha]^{25} = +70.41°$ (c=1.0, MeOH).

Analysis for $C_{18}H_{27}NO_2S$: Calculated: C, 67.25; H, 8.47; N, 4.36; Found: C, 66.95; H, 8.22; N, 4.26.

81.(−)-5-[[3,5-bis(1,1-dimethylethyl)-4-hydroxyphenyl]methyl]-4-thiazolidinone-1-oxide
m.p. 182°–184° C.

$[\alpha]^{25} = -21.84°$ (c=1.0, MeOH).

Analysis for $C_{18}H_{27}NO_3S$: Calculated: C, 64.06; H, 8.06; N, 4.15; Found: C, 63.84; H, 8.09; N, 4.12.

82. (+)-5-[[3,5-bis(1,1-dimethylethyl)-4-hydroxyphenyl]methyl]-4-thiazolidinone-1-oxide
m.p. 177°–181° C.

$[\alpha]^{25} = +163.05°$ (c=1.0, MeOH).

Analysis for $C_{18}H_{27}NO_3S$: Calculated: C, 64.06; H, 8.06; N, 4.15; Found: C, 63.88; H, 8.12; N, 4.29.

EXAMPLE 83

(−)-5-[[3,5-bis(1,1-dimethylethyl)-4-hydroxyphenyl]methyl]-3-methyl-4-thiazolidinone In a similar manner as that described in Example 79, 0.45 ml (1.5 mmol) of titanium isopropoxide, 0.63 ml (3.0 mmol) of (+)-diisopropyltartrate, 27 liter (1.5 mmol) of water, 0.84 g (2.5 mmol) of racemic 5-[[3,5-bis(1,1-dimethylethyl)-4-hydroxyphenyl]methyl]-3-methyl-4-thiazolidinone and 0.58 ml (1.5 mmol) of a 2.57M solution of t-butylhydroperoxide in isooctane were reacted to provide a residue. The residue was dissolved in 25 ml of methylene chloride and the resulting solution was chromatographed on a silica gel chromatography column. Elution with 1000 ml of methylene chloride, then 6000 ml of a 0–10% ethyl acetate in methylene chloride gradient, then 4000 ml of a 20–50% isopropyl alcohol in hexane gradient and then 2000 ml of a 50% isopropyl alcohol/hexane solution provided various fractions containing the above-titled compound. These fractions were combined and the liquid evaporated to provide 0.35 g of title compound.

Analysis for $C_{19}H_{29}NO_2S$: Calculated: C, 68.02; H, 8.71; N, 4.17; Found: C, 67.95; H, 8.55; N, 4.18.

NMR (300 MHz; CDCl) δ=1.4 (s,18H), 2.9 (s,3H), 3.0 (dd,1H), 3.3 (dd,1H), 3.8 (dd, 1H), 4.0 (d,1H), 4.2 (d,1H), 5.1 (s,1H), 7.1 (s,2H).

Utilizing the procedures set forth herein, the following additional compounds were prepared.

EXAMPLE 84

5-[[3,5-bis(1,1-dimethylethyl -4-hydroxyphenyl]methylene]-3-[(4-morpholinyl)methyl]-4-thiazolidinone, m.p. 204°–206° C. (dec.)

EXAMPLE 85

5-[[3,5-dimethoxy-4-hydroxyphenyl]methylene]-2-thioxo-3-methyl-4-thiazolidinone, m.p. 211°–213° C.

EXAMPLE 86

5-[[3,5-dimethoxy-4-hydroxyphenyl]methylene]-3-methyl-4-thiazolidinone, m.p. 207°–212° C.

EXAMPLE 87

5-[[3-(methylthiophenyl)-4-hydroxy-5-ethoxyphenyl]methylene]-4-thiazolidinone, m.p. 182°–184° C.

Analysis for $C_{19}H_{19}NO_3S_2$: Calculated: C, 61.10; H, 5.13; N, 3.75; S, 17.17; Found: C, 61.31; H, 5.07; N, 3.80; S, 17.44.

EXAMPLE 88

5-[[3-(methylthiophenyl)-4-hydroxy-5-ethoxyphenyl]methylene]-3-methyl-4-thiazolidinone, m.p. 142°–145° C.

Analysis for $C_{20}H_{21}NO_3S_2$: Calculated: C, 61.99; H, 5.46; N, 3.61; Found: C, 62.15; H, 5.68; N, 3.49.

EXAMPLE 89

5-[(4-hydroxyphenyl)methylene]-2-thioxo-4-thiazolidinone, m.p. 287°–290° C.

EXAMPLE 90

5-[(3-methoxy-4-hydroxyphenyl)methylene]-2-thioxo-4-thiazolidinone, m.p. 229°–231° C.

EXAMPLE 91

5-[(3-methoxy-4-hydroxyphenyl)methylene]-2-thioxo-3-(2-propenyl)-4-thiazolidinone.

EXAMPLE 92

5-[(3-ethoxy-4-hydroxyphenyl)methylene]-2-thioxo-4-thiazolidinone, m.p. 217°–217.5° C.

EXAMPLE 93

5-[[3,5-bis(1,1-dimethylethyl)-4-hydroxyphenyl]methylene]-4-oxo-2-thioxo-3-thiazolidine acetic acid, m.p. −265° C.

EXAMPLE 94

5-[(3,5-dimethyl-4-hydroxyphenyl)methylene]-2-thioxo-4-thiazolidinone, m.p. 260° C.

EXAMPLE 95

5-[(3,5-dimethoxy-4-hydroxyphenyl)methylene]-2-thioxo-4-thiazolidinone, m.p. 230° C.

EXAMPLE 96

5-[[3-(1,1-dimethylethyl)-4-hydroxy-5-(methylthiophenyl)phenyl]methylene]-2-thioxo-4-thiazolidinone, m.p. 181°–184° C.

EXAMPLE 97

5-[(3-ethoxy-4-hydroxyphenyl)methylene]-2-thioxo-3-cyclohexyl-4-thiazolidinone, m.p. 122°–123° C.

EXAMPLE 98

5-[(3-ethoxy-4-hydroxyphenyl)methylene]-2-thioxo-3-methyl-4-thiazolidinone, m.p. 157° C.

EXAMPLE 99

5-[[3,5-bis(1-methylpropyl)-4-hydroxyphenyl] methylene]-4-oxo-2-thioxo-3-thiazolidine acetic acid, m.p. 191°–193° C.

EXAMPLE 100

5-[[3,5-bis(1-methylethyl)-4-hydroxyphenyl]methylene]-3-methyl-4-thiazolidinone, m.p. 200°–210° C.

Analysis for $C_{17}H_{23}NO_2S$: Calculated: C, 66.85; H, 7.59; N, 4.59; Found: C, 67.03; H, 7.55; N, 4.37.

EXAMPLE 101

4-[[3,5-bis(1,1-dimethylethyl)-4-hydroxyphenyl]methylene]-1,3-oxothiolan-5-one

A. Preparation of β-(3,5-di-t-butyl-4-hydroxyphenyl)-α-mercaptoacrylic acid.

A solution of 174.5 g of 5-[[3,5-bis(1,1-dimethylethyl)-4-hydroxyphenyl]methylene]-2-thioxo-4-thiazolidinone in 1250 ml of a 10% sodium hydroxide solution was heated on a steam bath for four hours. Decolorizing carbon was added and the mixture filtered through a high flow diatomaceous earth pad. The filtrate was chilled by adding ice and treated with 6N hydrochloric acid. The precipitated product was recovered by filtration, washed with water, and dried providing 150 g of the desired subtitled intermediate.

B. Preparation of 4-[[3,5-bis(1,1-dimethylethyl)-4-hydroxyphenyl]methylene]-1,3-oxothiolan-5-one.

Following the procedure of Agr. Biol. Chem., 29(8), 728 (1965), six grams of the mercaptoacrylic acid from above were heated on a steam bath with 36 ml of acetic acid and 6 ml of formaldehyde (37% solution) for one hour. Evaporation of the mixture and chromatography of the residue over silica gel provided 1.7 g of the desired product, m.p. 127°–129° C.

Analysis for $C_{18}H_{24}O_3S$: Calculated: C, 67.47; H, 7.55; Found: C, 67.71; H, 7.62.

As noted previously, the compounds of formula I are useful for treating multiple sclerosis. Such activity was demonstrated in the following test system.

Experimental Autoimmune Encephalomyelitis (EAE) Model

Experimental autoimmune encephalomyelitis (EAE) is an inflammatory autoimmune demyelinating disease which can be induced in laboratory animals by injection of myelin basic protein. Such disease has become the standard laboratory model for studying clinical and experimental autoimmune diseases. In fact, numerous articles [e.g., Abramsky, et al., J. Neuroimmunol., 2, 1 (1982) and Bolton et al., J. Neurol. Sci., 56, 147 (1982)] note that the similarities of chronic relapsing EAE in animals to multiple sclerosis in humans especially implicates the value of EAE for the study of autoimmune demyelinating diseases such as multiple sclerosis. As such, the EAE test model was employed to establish the activity of the compounds of formula I against multiple sclerosis. Such testing was conducted according to the following procedure.

Female Lewis rats (Olac Ltd., U. K.), were injected in their footpads with 12.5 μg of myelin basic protein (MBP) (prepared form guinea-pig spinal cord) in Complete Freunds adjuvant. Test compound was given daily from day 0 (MBP injection date) in carboxymethylcellulose p.o. at a dosage of 33 mg/kg to the test animals. A control solution (carboxymethylcellulose alone) was given to certain other test animals. The animals were then weighed and scored daily for symptoms of EAE according to a scale of 0 to 3 (0=no change; 1=flaccid tail; 2=hind limb disability and 3=hind quarter paralysis/moribund). Animals were sacrificed when they reached a score of 3.

The results of the experiment described above are set forth in Table I, below. In Table I, Column 1 indicates the example number of the test compound employed or, if appropriate, that no test compound was employed (control). Columns 2–16 report the EAE disease score associated with various times after the MBP injection date (day 0).

TABLE I

| Compound Example No./ | Inhibition of EAE | | | | | | | | | | | | | | |
|---|---|---|---|---|---|---|---|---|---|---|---|---|---|---|---|
| | EAE Disease Score At Various Days After MBP Administration* | | | | | | | | | | | | | | |
| Control | 1 | 2 | 3 | 4 | 5 | 6 | 7 | 8 | 9 | 10 | 11 | 12 | 13 | 14 | 15 |
| Control | 0 | 0 | 0 | 0 | 0 | 0 | 0 | 0 | 0 | 0 | 0.5 | 1.5 | 2.2 | 2.7 | 2.8 |
| Example 21 | 0 | 0 | 0 | 0 | 0 | 0 | 0 | 0 | 0 | 0 | 0.5 | 1.8 | 2.3 | 2.5 | 2.5 |
| Example 2 | 0 | 0 | 0 | 0 | 0 | 0 | 0 | 0 | 0 | 0 | 0.3 | 1.5 | 2.8 | 3.0 | 3.0 |
| Example 10 | 0 | 0 | 0 | 0 | 0 | 0 | 0 | 0 | 0 | 0 | 0 | 0.1 | 2.0 | 2.7 | 3.0 |

*EAE Disease Score based on an average of 6 test animals.

The results set forth in Table I, above, establish that, given the proper dosing paradigm, the compounds of formula I inhibit the progression of EAE. In particular, the compound of Example 10 delayed onset of the disease for at least 1 day relative to control. As such, the compounds of formula I would be expected to be efficacious in treating multiple sclerosis.

As noted above, the compounds of formula I are capable of slowing the process of neurodegeneration associated with multiple sclerosis, thereby lending themselves to the valuable therapeutic method claimed herein. This method comprises administering to a mammal in need of treatment for multiple sclerosis an amount of one or more compounds of formula I sufficient to achieve the therapeutic effect desired. The compounds can be administered by a variety of routes including the oral, rectal, transdermal, subcutaneous, intravenous, intramuscular or intranasal routes. The oral and transdermal routes of administration are preferred. No matter what route of administration is chosen, such administration is accomplished by means of pharmaceutical compositions which are prepared by techniques well known in the pharmaceutical sciences.

In making the pharmaceutical compositions, one or more active ingredients will usually be mixed with a carrier, or diluted by a carrier, or enclosed within a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium , ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrroiidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more suitable pharmaceutical diluents, excipients or carriers.

The compounds utilized in the method of the present invention are effective over a wide dosage range for the treatment of multiple sclerosis. Thus, as used herein, the term "therapeutically effective amount" refers to a dosage range of from about 0.5 to about 500 mg/kg of body weight per day. In the treatment of adult humans, the range of about 1 to about 100 mg/kg, in single or divided doses, is preferred. However, it will be understood that the amount of the compound actually administered will be determined by a physician, in the light of the relevant circumstances including the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active ingredients any of the compounds of formula I. The examples are illustrative only and are not intended to limit the scope of the invention in any way.

EXAMPLE 102

Hard gelatin capsules are prepared using the following ingredients:

|  | Quantity (mg/capsule) |
| --- | --- |
| Compound of Example 10 | 250 |
| Starch dried | 200 |
| Magnesium | 10 |

The above ingredients are mixed and filled into hard gelatin capsules in 460 mg quantities.

EXAMPLE 103

A tablet formula is prepared using the ingredients below:

|  | Quantity (mg/tablet) |
| --- | --- |
| Compound of Example 21 | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 104

An aerosol solution is prepared containing the following components:

|  | Weight % |
| --- | --- |
| Compound of Example 101 | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 105

Tablets each containing 60 mg of active ingredient are made up as follows:

| | |
|---|---|
| Compound of Example 47 | 60 mg |
| Starch | 45 mg |
| Microcrystalline cellulose | 35 mg |
| Polyvinylpyrrolidone (as 10% solution in water | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. Sieve, are then added to the granules which, after mixing, are compressed by a tablet machine to yield tablets each weighing 150 mg.

EXAMPLE 106

Capsules each containing 80 mg of medicament are made as follows:

| | |
|---|---|
| Compound of Example 35 | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 107

Suppositories each containing 225 mg of active ingredient are made up as follows:

| | |
|---|---|
| Compound of Example 50 | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 108

Suspensions each containing 50 mg of medicament per 5 ml dose are made as follows:

| | |
|---|---|
| Compound of Example 54 | 50 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 109

Capsules each containing 150 mg of medicament are made up as follows:

| | |
|---|---|
| Compound of Example 10 | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

We claim:

1. A method for treating multiple sclerosis in a mammal in need of such treatment which comprises administering to said mammal a therapeutically effective amount of a compound, or pharmaceutically acceptable salt thereof, of the formula (I)

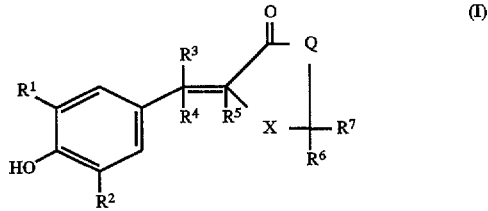

wherein:

$R^1$ and $R^2$ are each independently hydrogen, $C_1-C_6$ alkyl, $C_1-C_6$ alkoxy, $C_2-C_6$ alkenyl, $C_2-C_6$ alkynyl or

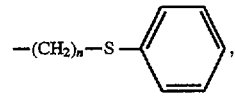

where n is an integer from 0 to 3, both inclusive;

$R^3$ is hydrogen or $C_1-C_6$ alkyl;

$R^4$ and $R^5$ are each hydrogen, or when taken together form a bond;

$R^6$ and $R^7$ are each hydrogen or when taken together are =S, or when one of $R^6$ and $R^7$ is hydrogen, the other is —$SCH_3$;

X is

where m is 0, 1 or 2;

Q is —O— or $NR^8$; and $R^8$ is hydrogen, $C_1$–$C_6$, $C_3$–$C_8$ cycloalkyl, $C_2$–$C_6$ alkenyl, —$SO_2CH_3$ or —$(CH_2)_n$—Y, where n is an integer from 0 to 3, both inclusive, and Y is cyano, $OR^9$,

tetrazolyl, —$NR^{11}R^{12}$, —SH, —S($C_1$–$C_4$ alkyl) or

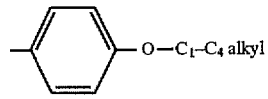

where $R^9$ is hydrogen, $C_1$–$C_4$ alkyl, tosyl or

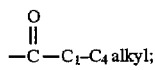

$R^{10}$ is hydroxy, $C_1$–$C_4$ alkyl, $C_1$–$C_4$ alkoxy or —$NH_2$; $R^{11}$ and $R^{12}$ are each independently hydrogen, $C_1$–$C_6$ alkyl, $C_2$–$C_6$ alkenyl, $C_2$–$C_6$ alkynyl, —$(CH_2)_qOH$, —$(CH_2)_qN(C_1$–$C_4$ alkyl$)_2$, —$(CH_2)_qS(C_1$–$C_4$ alkyl) or

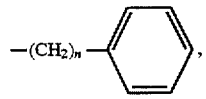

where q is an integer from 1 to 6, both inclusive, and n is as defined above; or $R^{11}$ and $R^{12}$ taken together form a morpholinyl, piperidinyl, piperazinyl or N-methylpiperazinyl ring.

2. A method of claim 1 which employs a compound of formula I wherein Q is —$NR^8$ and $R^8$ is hydrogen, $C_1$–$C_6$ alkyl, $C_3$–$C_8$ cycloalkyl or $(CH_2)_n$—Y, where n is an integer from 0 to 3, both inclusive, and Y is $OR^9$,

—$NR^{11}R^{12}$ or

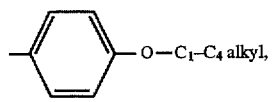

where $R^9$, $R^{10}$, $R^{11}$ and $R^{12}$ are as defined in claim 1.

3. A method of claim 2 which employs a compound of formula I wherein $R^3$ is hydrogen.

4. A method of claim 3 which employs a compound of formula I wherein X is

where m is 0.

5. A method of claim 4 which employs a compound of formula I wherein $R^6$ and $R^7$ are each hydrogen or when taken together are =S.

6. A method of claim 5 which employs a compound of formula I wherein $R^1$ and $R^2$ are each independently $C_1$–$C_6$ alkyl, $C_1$–$C_6$ alkoxy or

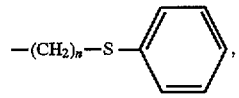

where n is 1,2 or 3.

7. A method of claim 6 which employs a compound of formula I wherein Q is —$NR^8$ and $R^8$ is hydrogen, $C_1$–$C_6$ alkyl or —$(CH_2)_n$—Y, where n is 0, 1 or 2, and Y is $OR^9$ ($R^9$ being hydrogen or $C_1$–$C_4$ alkyl) or —$NR^{11}R^{12}$ [$R^{11}$ and $R^{12}$ each being independently hydrogen, $C_1$–$C_6$ alkyl or —$(CH_2)_qOH$, where q is 1, 2 or 3].

8. A method of claim 7 which employs a compound of formula I wherein $R^4$ and $R^5$ taken together form a bond.

9. A method of claim 8 which employs a compound of formula I wherein $R^6$ and $R^7$ are both hydrogen.

10. A method of claim 9 which employs a compound of formula I wherein Q is $NR^8$ and $R^8$ is hydrogen, $C_1$–$C_4$ alkyl or —$(CH_2)_n$—Y, where n is 0, 1 or 2, and Y is hydroxy or $NR^{11}R^{12}$ [$R^{11}$ and $R^{12}$ each being independently hydrogen, methyl or —$(CH_2)_2OH$].

11. A method of claim 10 which employs a compound of formula I wherein $R^1$ and $R^2$ are each independently $C_1$–$C_6$ alkyl or

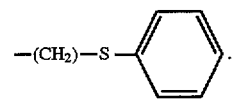

12. A method of claim 11 which employs a compound of formula I wherein $R^1$ and $R^2$ are both 1,1-dimethylethyl.

13. A method of claim 11 which employs a compound wherein Q is $NR^8$ and $R^8$ is $C_1$–$C_4$ alkyl.

14. The method of claim 13 which employs 5-[[3,5-bis (1,1-dimethylethyl)-4-hydroxyphenyl]methylene]-3-methyl-4-thiazolidinone.

15. The method of claim 12 which employs 5-[[3,5-bis (1,1-dimethylethyl)-4-hydroxyphenyl]methylene]-3-(dimethylamino)-4-thiazolidinone.

16. The method of claim 12 which employs 5-[[3,5-bis (1,1-dimethylethyl)-4-hydroxyphenyl]methylene]-3-(methylamino)-4-thiazolidinone.

17. The method of claim 12 which employs 5-[[3,5-bis (1,1-dimethylethyl-4-hydroxyphenyl]methylene]-3-(2-hydroxyethyl)-4-thiazolidinone.

18. The method of claim 12 which employs 5-[[3,5-bis (1,1-dimethylethyl)-4-hydroxyphenyl]methylene]-3-amino-4-thiazolidinone.

19. The method of claim 12 which employs 5-[[3,5-bis (1,1-dimethylethyl)-4-hydroxyphenyl]methylene]-3-[(2-hydroxyethyl)amino]-4-thiazolidinone.

20. The method of claim 1 which employs 4-[[3,5-bis(1,1-dimethylethyl)-4-hydroxyphenyl]methylene]-1,3-oxothiolan-5-one.

* * * * *